(12) United States Patent
Ophardt et al.

(10) Patent No.: US 8,816,860 B2
(45) Date of Patent: Aug. 26, 2014

(54) DISPENSER WITH SOUND GENERATORS

(75) Inventors: Heiner Ophardt, Arisdorf (CH); Tony Kortleve-Snider, Beamsville (CA)

(73) Assignee: Gotohti.com Inc., Beamsville (CA)

( * ) Notice: Subject to any disclaimer, the term of this patent is extended or adjusted under 35 U.S.C. 154(b) by 18 days.

(21) Appl. No.: 13/441,700

(22) Filed: Apr. 6, 2012

(65) Prior Publication Data

US 2013/0099929 A1    Apr. 25, 2013

(30) Foreign Application Priority Data

Apr. 8, 2011  (CA) .................................... 2737012
Mar. 6, 2012  (CA) .................................... 2770704

(51) Int. Cl.
*G08B 23/00*  (2006.01)
*A47K 5/12*   (2006.01)
*G08B 3/10*   (2006.01)

(52) U.S. Cl.
USPC .............. 340/573.1; 340/286.07; 340/286.09; 340/539.11; 222/23; 222/27; 222/39; 222/52; 221/9; 221/96

(58) Field of Classification Search
CPC ........... G08B 21/245; A47K 7/00; A47K 5/00
See application file for complete search history.

(56) References Cited

U.S. PATENT DOCUMENTS

| | | | |
|---|---|---|---|
| 724,545 A | 4/1903 | Conklin | |
| 3,538,637 A | 11/1970 | Smith | |
| 4,674,654 A * | 6/1987 | Fujii et al. | 222/39 |
| 5,165,577 A | 11/1992 | Ophardt | |
| 5,816,186 A | 10/1998 | Shepherd | |
| 5,927,548 A | 7/1999 | Villaveces | |
| 6,698,377 B1 * | 3/2004 | Topman et al. | 116/137 R |
| 7,367,477 B2 | 5/2008 | Ophardt | |
| 7,708,166 B2 * | 5/2010 | Ophardt | 222/190 |
| 7,898,407 B2 | 3/2011 | Hufton | |
| 7,984,831 B2 | 7/2011 | Kanfer | |
| 8,033,201 B2 | 10/2011 | Cutler | |
| 8,071,933 B2 | 12/2011 | Ophardt | |
| 8,074,844 B2 | 12/2011 | Ophardt | |
| 8,264,343 B2 * | 9/2012 | Snodgrass | 340/539.16 |
| 2008/0020794 A1 | 1/2008 | Garon et al. | |
| 2009/0114679 A1 | 5/2009 | Ophardt | |
| 2009/0166381 A1 | 7/2009 | Phelps et al. | |
| 2009/0261123 A1 * | 10/2009 | McNiff et al. | 222/39 |
| 2010/0073162 A1 | 3/2010 | Johnson et al. | |
| 2010/0117836 A1 | 5/2010 | Seyed Momen | |
| 2010/0288788 A1 | 11/2010 | Ophardt | |
| 2011/0005606 A1 | 1/2011 | Bartels | |

(Continued)

FOREIGN PATENT DOCUMENTS

| | | |
|---|---|---|
| EP | 2223642 | 9/2010 |
| GB | 2425388 | 10/2006 |

*Primary Examiner* — Benjamin C Lee
*Assistant Examiner* — Rajsheed Black-Childress
(74) *Attorney, Agent, or Firm* — Thorpe North & Western LLP

(57) ABSTRACT

In combination a fluid dispenser for dispensing fluid and a sound sensing mechanism remote from the fluid dispenser, the fluid dispenser dispensing fluid when activated, the fluid dispenser including a sound generator which generates a sound when the fluid dispenser is activated, the sound sensing mechanism separate from and spaced from the fluid dispenser, the sound sensing mechanism including a sound sensor to sense the sound generated by the sound generator, the sound sensing mechanism including a communication system to transmit data representative of the sound sensed by the sound generator.

17 Claims, 24 Drawing Sheets

(56) References Cited

U.S. PATENT DOCUMENTS

| | | | |
|---|---|---|---|
| 2011/0011886 A1* | 1/2011 | Zaima et al. | 222/1 |
| 2011/0169646 A1 | 7/2011 | Raichman | |
| 2012/0112914 A1* | 5/2012 | Wegelin et al. | 340/573.1 |
| 2012/0194338 A1* | 8/2012 | Snodgrass | 340/539.12 |
| 2012/0212344 A1 | 8/2012 | Forsberg et al. | |
| 2013/0033376 A1 | 2/2013 | Seyed Momen | |
| 2013/0126554 A1 | 5/2013 | Ophardt et al. | |

* cited by examiner

DISPENSER WITH SOUND GENERATORS

SCOPE OF THE INVENTION

This invention relates to dispensers particularly hand cleaning fluid dispensers and particularly to apparatus and methods for compliance monitoring of the use of such dispensers.

BACKGROUND OF THE INVENTION

The present inventors have appreciated that proper compliance monitoring of hand washing requires monitoring of all hand cleaning fluid dispensers within any particular facility or environment to be monitored. The present inventors have also appreciated that for practical compliance monitoring, the delivery of data regarding the usage of individual dispensers preferably is automatically communicated to a central computer system. Previously known dispensers which are useful for automatic compliance monitoring require a source of electric power to drive an electronic apparatus which can be used to generate signals and/or data regarding the operation of the dispenser and communicate the same such that the data may be received by a computer system.

The present inventors have appreciated the disadvantage that many previously known fluid dispensers in use do not have any electrical power source or electronic componentry which permits the dispensers to record or communicate usage data about that dispenser.

The present inventors have appreciated the disadvantage that most known hand washing compliance monitoring systems do not monitor all dispensers in a facility.

SUMMARY OF THE INVENTION

To at least partially overcome these disadvantages of previously known devices, the present invention provides a fluid dispenser with a sound generator which generates a sound when the fluid dispenser is activated by a user and, as well, the present invention provides in combination with such a fluid dispenser, a sound sensing mechanism separate from and spaced from the fluid dispenser which senses the sound generated by the sound generator with the sound sensing mechanism including a communications system for relay of data representing sound sensed by the sound generator.

An object of the present invention is to provide a fluid dispenser including a sound generator which generates a sound when the fluid dispenser is activated.

Another object is to provide a combination of a fluid dispenser for dispensing fluid which generates a sound when fluid is dispensed from the dispenser and a sound sensing mechanism remote from the fluid dispenser to sense a sound generated by the sound generator.

Another object is to provide an apparatus and method for compliance monitoring of fluid dispensers by sensing sound generated from fluid dispensers when fluid is dispensed.

According to one aspect, the present invention provides in combination a fluid dispenser for dispensing fluid and a sound sensing mechanism remote from the fluid dispenser,
  the fluid dispenser dispensing fluid when activated,
  the fluid dispenser including a sound generator which generates a sound when the fluid dispenser is activated,
  the sound sensing mechanism separate from and spaced from the fluid dispenser,
  the sound sensing mechanism including a sound sensor to sense the sound generated by the sound generator,
  the sound sensing mechanism including a communication system to transmit data representative of the sound sensed by the sound generator.

According to another aspect, the present invention provides a method of compliance monitoring of hand washing within a facility comprising:
  producing a sound each time a dispenser is activate,
  remotely monitoring the sounds produced by one or more sound sensors positioned to receive sounds,
  transmitting data representative of the sounds sensed by the sound sensors to a central computer.

In another aspect, the present invention provides a personal hand hygiene compliance unit carried on a person for compliance monitoring of hand hygiene. The unit comprising a hand sanitizing fluid dispenser and a communication enabled, not larger than pocket-sized personal computer which is preferably portable and handheld. The dispenser comprises a dispenser housing, a reservoir for containing a fluid, a pump and a discharge outlet. The dispenser housing carries the reservoir, the pump and the discharge outlet. The pump may be an electrically powered pump or a pump which uses manual power to dispense fluid. The pump is coupled to the reservoir with the pump in communication with the fluid in the reservoir. The pump is capable of being activated to dispense the fluid from the reservoir out the discharge outlet. The pocket-sized personal computer has a computer housing, and within the computer housing, a controller, a user interface, a battery and a data communication device for transmission of data from the pocket-sized personal computer. The pump may comprise an electrically powered pump or a pump which uses manual power to dispense fluid. In one configuration, the pump when activated generates a sound and the personal computer acts as sound sensing mechanism to sense the sound and communicate the sensing of the sound to a central computer system. The personal computer may communicate that the pump has been activated to the central computer system by generating another sound to be picked up by a sound sensing mechanism. The controller may monitor when the pump is activated by sensing sound or by other sensors and may provide for communication of data regarding the activation of the pump to a remote computer for compliance monitoring by generation of sound or other wireless communication signals such as WiFi signals.

BRIEF DESCRIPTION OF THE DRAWINGS

Further aspects and advantages of the present invention will become apparent from the following description taken together with the accompanying drawings in which.

DETAILED DESCRIPTION OF THE DRAWINGS

Figure 1:
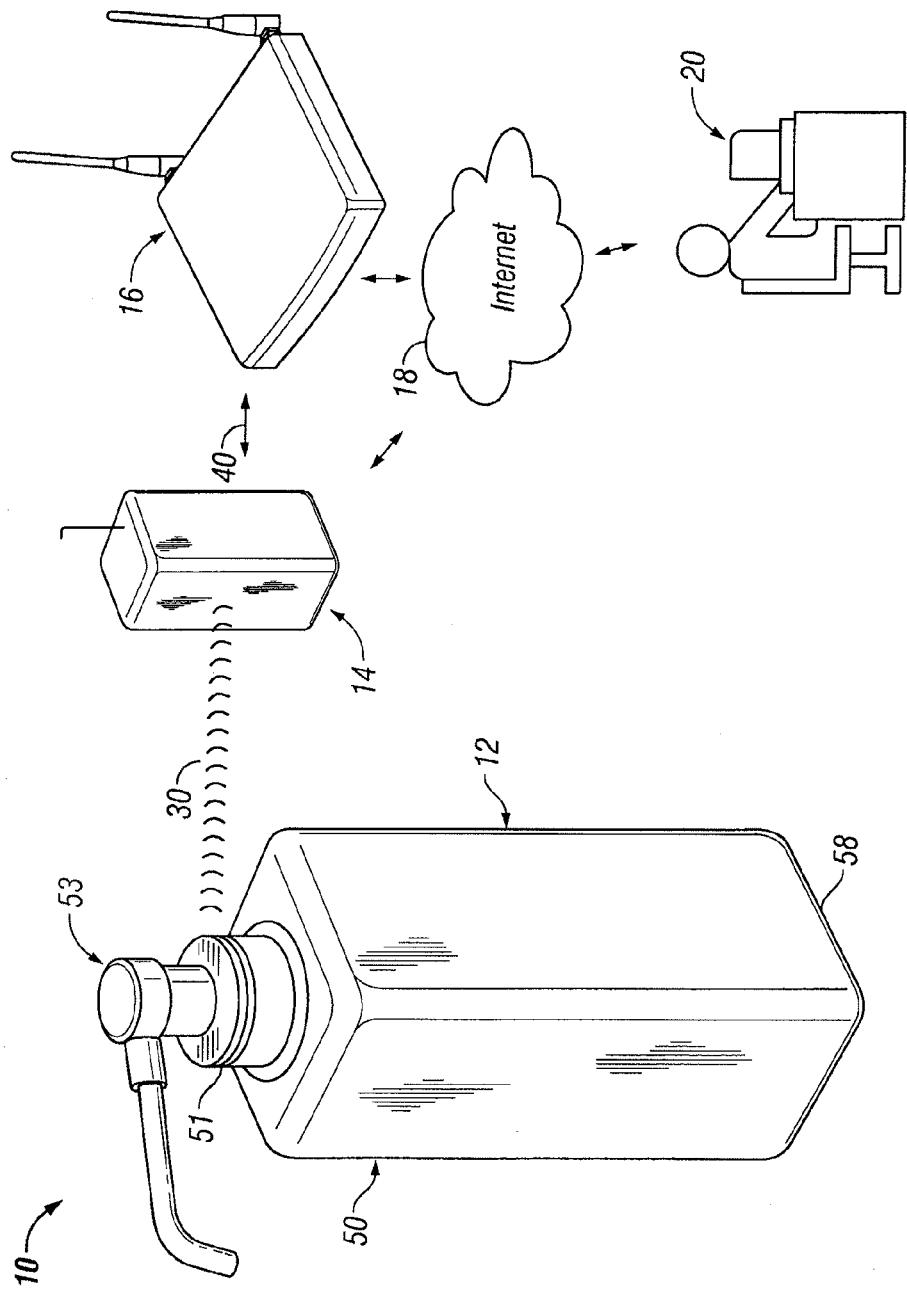
FIG. 1 is a schematic view of a compliance monitoring apparatus in accordance with a first embodiment of the present invention.

Reference is made to FIG. 1 which schematically illustrates a simplified version of a compliance monitoring apparatus 10 in accordance with the present invention which includes one sound producing fluid dispenser 12 herein often referred to as a sounding dispenser 12, one sound sensing mechanism 14, and one wireless router 16. The wireless router 16 is shown as being connected to the Internet 18 and via the Internet 18 to a computing system 20.

Figure 2:
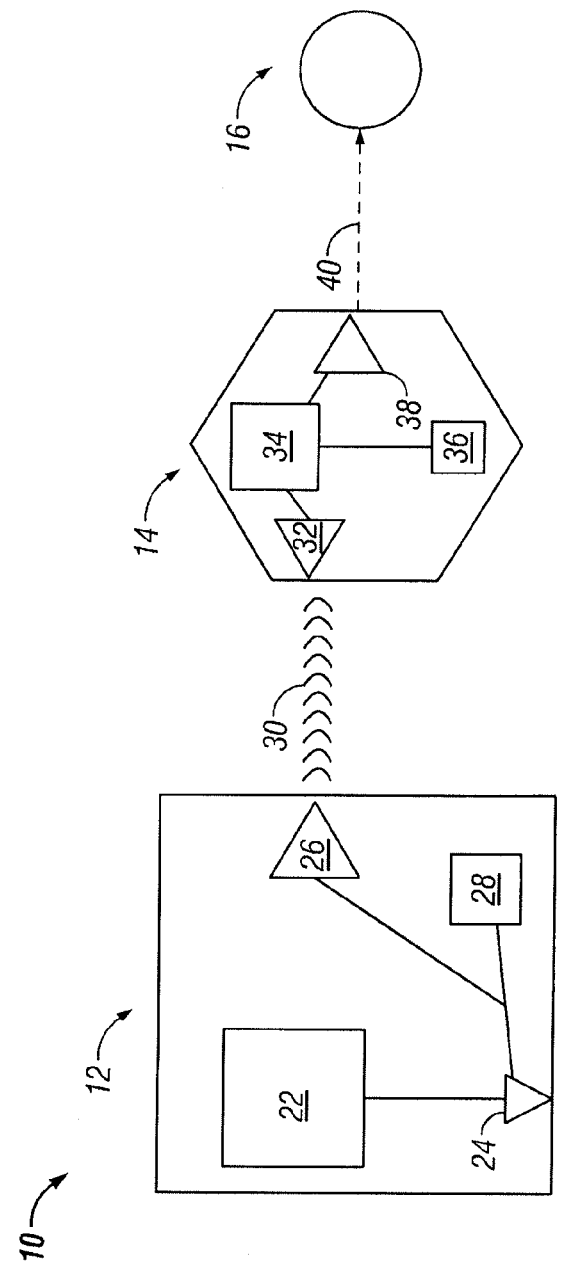
FIG. 2 is a schematic pictorial view of a combination of the one exemplary sound generating fluid dispenser, the one exemplary sound sensing mechanism and the one exemplary router shown in FIG. 1.

As seen in the schematic flowchart in FIG. 2, the sounding dispenser 12 includes a fluid reservoir 22, a pump mechanism 24 to dispense fluid from the reservoir 22, an activator 28 to activate the pump mechanism 24 and a sound generator 26 to generate sound 30 when the sounding dispenser 12 is activated or fluid is dispensed by the sounding dispenser 12.

The sound sensing mechanism 14 includes a sound sensor 32, an electrically powered controller 34 to control the operation of the sound sensing mechanism, an electrical power source 36 and a communications mechanism 38. The sound sensor 32 senses the sound 30 and provides input to the controller 34 which assesses the input and appropriately develops data or output which is communicated by the communication mechanism 38 as wireless signals 40 to the wireless router 16.

Figure 3:
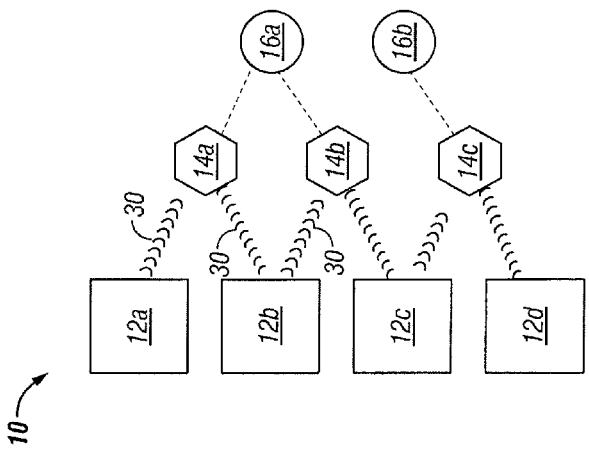
FIG. 3 is a schematic flowchart showing one configuration of components of a compliance monitoring apparatus in accordance with the first embodiment of the invention as shown in FIG. 1, however, including multiple sound generating fluid dispensers, sound sensing mechanisms and routers.

For ease of illustration in the assembly 10 of FIG. 1 only one sounding dispenser 12, one sound sensing mechanism 14, and one wireless router 16 are shown however a plurality of each may preferably be provided. FIG. 3 illustrates a simplified version of a compliance monitoring apparatus 10 in accordance with the first embodiment of the present invention which is the same as that of FIG. 1 but which includes four sounding dispensers 12 indicated as 12a, 12b, 12c and 12d, three sound sensing mechanisms 14 indicated as 14a, 14b and 14c, and two wireless routers 16 indicated as 16a and 16b. The number of each of the sounding dispensers 12, sound sensing mechanisms 14 and wireless routers 16 is not limited. Each of the sounding dispensers 12 is adapted to generate a sound 30 when the fluid dispenser 12 is activated to dispense fluid or fluid is dispensed. The sound 30 generated by each sounding dispenser 12 is schematically illustrated as moving from the respective sounding dispenser 12 to one or more of the sound sensing mechanisms 14. Each sound sensing mechanism 14 has the capability to sense the sound 30 and to communicate data representative of the sound 30 sensed as signals 40 to one or more of the wireless routers 16.

FIG. 3 shows the sound 30 from sounding dispenser 12b being received by both sound sensing mechanism 14a and sound sensing mechanism 14b. The apparatus 10 is provided with a mechanism for determining when sound 30 representative of a single activation of one sounding dispenser 12 may be sensed by multiple sound sensing mechanisms 14. Preferably, the controller 34 in each sound sensing mechanism 14 will have a real time clock which will permit the output 40 representative of each duplicated sound sensing to be identified at least by time such that the computing system 20 may recognize duplicate sensing of sound 30 from a single activation of one sounding dispenser 12 by multiple of the sound sensing mechanisms 14.

In accordance with the present invention, the compliance monitoring apparatus 10 preferably provides monitoring for each and every hand cleaning fluid dispenser within an a specified location or a facility, preferably with information about the operation about every fluid dispenser communicated to the computing system 20. The specified location or a facility may be, for example, a hospital or food preparation facility or any designated area within such a location or facility. Dispensers within the compliance monitoring apparatus 10 can include not only sounding dispensers 12 as, for example, shown in FIGS. 1 to 3, but also other non-sounding dispensers which do not produce sounds when fluid is dispensed and are connected to the computing system 20 by a different mechanism.

Figure 4:
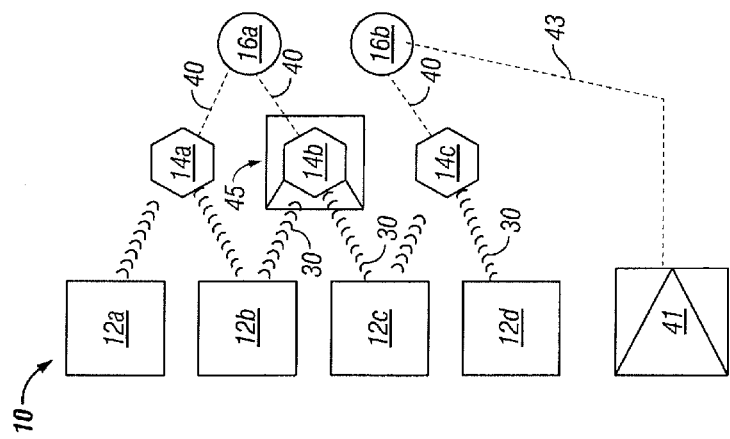
FIG. 4 is a schematic flowchart showing a compliance monitoring apparatus in accordance with a second embodiment of the present invention.

Reference is made to FIG. 4 which shows a modification of the apparatus of FIG. 3 to show a second embodiment of the apparatus 10 including one non-sounding dispenser 41. This non-sounding dispenser 41 shown in FIG. 4 is provided with a capability to wirelessly transmit information about its operation via wireless signals 43 directly to one of the wireless routers 16b. Such a non-sounding dispenser 41 is known and preferably includes electronic componentry similar to that in the sound sensing mechanism 14, that is, analogous to the sound sensor 32, the non-sounding dispenser 41 has some form of sensor to sense activation of the pump or dispensing of fluid, a controller, a power source and a communicating mechanism. The non-sounding dispenser 41, for example, may be automatically operated touch free with dispensing on the presence of a user's hand being sensed and by an electrically controlled pump as, for example, disclosed in U.S. Pat. No. 8,071,933 to Ophardt et al, issued Dec. 6, 2011, the disclosure of which is incorporated herein by reference. The non-sounding dispenser 41 could also be, for example, manually operated with manual power to operate the pump but with electronic componentry to transmit data wirelessly such as is disclosed in the U.S. Patent Publication US 2010/0288788 to Ophardt, published Nov. 18, 2010, the disclosure of which is incorporated herein by reference. There is no limit as to the nature of the non-sounding dispenser 41 other than that suitable data about its operation is communicated to the computing system 20. One or more non-sounding dispensers 41 can be incorporated into the compliance monitoring apparatus 10 in accordance with the present invention, preferably with information about the operation of these non-sounding dispensers 41 communicated to the computing system 20 at some time and by some manner that information from all the monitored dispensers whether sounding dispensers 12 or non-sounding dispensers 41 can preferably be consolidated. While FIG. 4 shows an apparatus 10 with but one non-sounding dispenser 41, one or more of such non-sounding dispensers 41 may be included in the apparatus 10.

One or more of the sound sensing mechanisms 14 may carry out functions other than the sensing of the sound 30 and providing output signals 40. For example, as seen in the apparatus 10 of FIG. 4, a hybrid sensor dispenser 45 is provided which is a combination of, and provides the capabilities of, both a sound sensing mechanism 14b and a non-sounding dispenser 41, such that the sound sensing mechanism 14b senses the sound 30 from sounding dispensers 12a and 12b and the hybrid sensor dispenser 45 transmits as its wireless signal 40 not only information about the operation of sounding dispensers 12a and 12b but also information about the operation of dispensing of fluid by a pump in the hybrid sensor dispenser 45.

Figure 5:
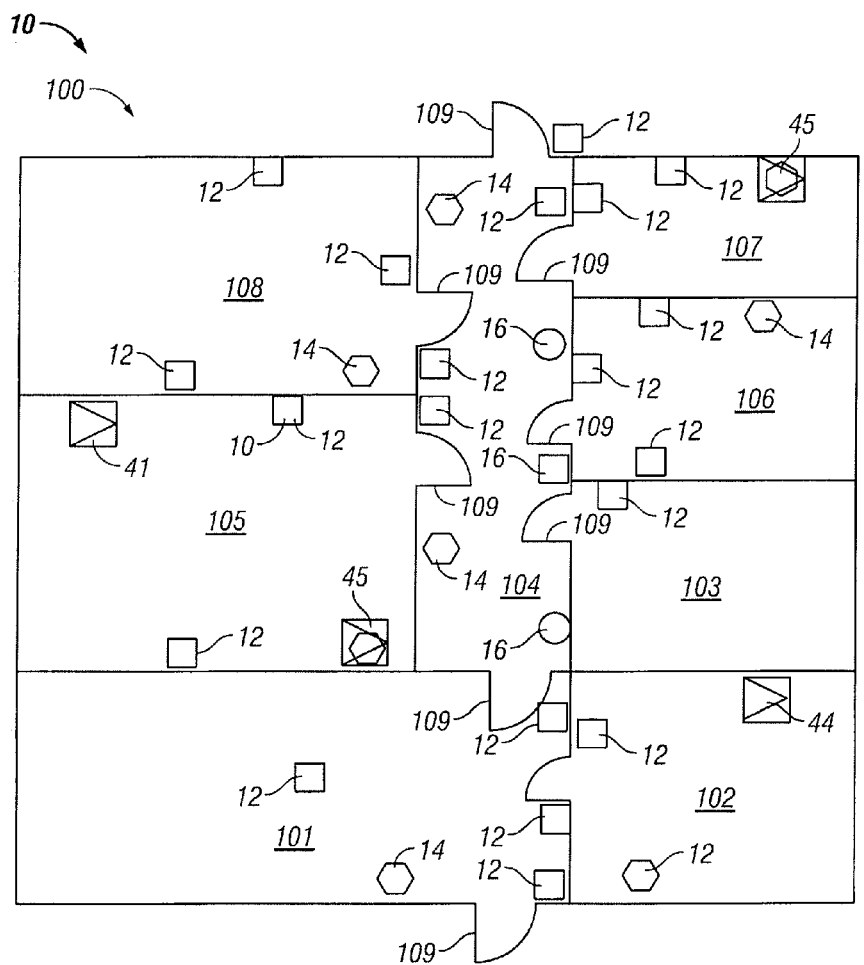
FIG. 5 is plan view of a health care facility having an array of dispensers in a compliance monitoring apparatus in accordance with the second embodiment of the present invention.

Reference is made to FIG. 5 which shows a plan view of a compliance monitoring apparatus 10 in accordance with the present invention installed in a health care facility 100. The facility 100 has a number of areas and rooms indicated as 101 to 108 with passage there between permitted by doors 109. FIG. 5 shows a plurality of different sounding dispensers 12, sound sensing mechanisms 14, and wireless routers 16 located at different locations within the facility 100, as well as two non-sounding dispensers 41 and two hybrid sensor dispensers 45. These communicating dispensers whether sounding dispensers 12, non-sounding dispensers 41 or hybrid sensor dispensers 45, are located at various different locations including those near the entry or exit of most doors 109, and within the rooms. These communicating dispensers may be carried by personnel, mounted to the walls, on freestanding supports or supported on desktops, countertops, and movable carts, and the like without limitation. Multiple of these communicating dispensers may be in any room as, for example, in a washroom with multiple toilets or sinks or wash stations, not shown or in a room for a plurality of patients with at least one dispenser per patient. By example, each room is shown to have at least one sounding dispenser 12. By example, each room other than room 103 has either a sound sensing mechanism 14 or a hybrid sensor dispenser 45 to sense sound from the sounding dispensers 12 in the same room. The room 104, which acts as a hallway, has two sound sensing mechanisms 14, and two wireless routers 16. One sound sensing mechanism 14 is located in the hallway room 104 proximate to the doorway 109 into room 103 to sense sound from the sounding dispenser 12 in room 103. Another sound sensing mechanism 14 is in the hallway room 104 proximate to the doorway 109 at the upper end of the hallway room 104 to sense sound from the sounding dispenser 12 outside of the rooms near the doorway 109 at the upper end of the hallway room 104.

The nature of the sound 30 produced by a particular dispenser 12, the sensitivity of any sound sensing mechanism 14 or hybrid sensor dispenser 45 to the sound 30, the location of walls, doors, curtains and other physical elements in a facility, the ability of the sound 30 to pass through air, as well as, for example, through walls, doors, curtains and other physical elements in a facility will have a bearing on where the sounding dispensers 12 and the sound sensing mechanism 14 or hybrid sensor dispenser 45 are placed in a facility to ensure that the sound 30 from every sounding dispensers 12 is sensed.

The particular nature of the sound generator 26 to be provided in each sounding dispenser 12 is not limited.

The sound generator 26 is to generate the sound 30 which is adapted to be sensed by one or more of the sound sensing mechanisms 14. The sound 30 is preferably transmitted through the air within the facility as within one or more air connected rooms in a facility, however, the sound 30 may also pass through curtains, walls, doors and other barriers within a facility as, for example, to be received by sound sensing mechanisms 14 in other rooms and other than by merely transmission through air in the facility.

The sound 30 may be of any frequency or magnitude. Preferably, the sound 30 may be of frequencies which are not heard by the human ear. The human ear typically may hear sound with frequencies in the range of about 20 Hz to about 20 k Hz. Preferably, the sound 30 is ultrasonic sound as with frequencies above 20 k Hz, preferably, above 50 k Hz, an approximate upper range for the hearing of dogs. A preferred range of ultrasonic frequencies is about 18 k Hz to 100 k Hz, more preferably about 18 k Hz to 22 k Hz or 50 k Hz to 60 k Hz. Infrasound frequencies may be utilized, being sounds with frequencies below 20 Hz, as can human audible sounds in the range of about 20 Hz to 20 k Hz.

Figure 6:
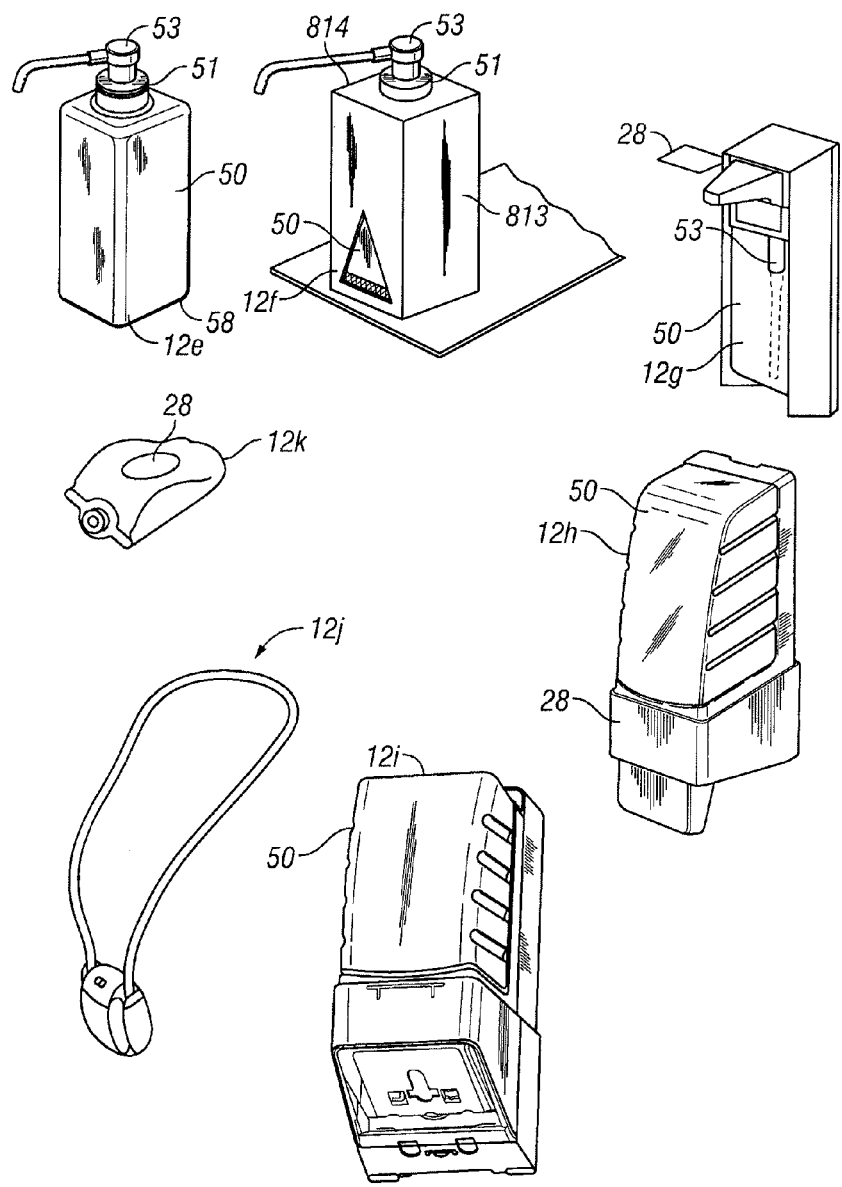
FIG. 6 is a collage showing pictorial views of seven different exemplary sound generating dispensers which may be used in accordance with the present invention.

The particular nature of dispensers which are useful as sounding dispensers 12 is not limited provided they dispense fluid and generate the sound 30. FIG. 6 shows a collage of known fluid dispensers which are modified to be sounding dispensers 12e to 12k in accordance with the present invention.

The sounding dispensers schematically illustrated as dispensers 12e and 12f in FIG. 3 are upstanding manually operated bottle dispensers that can be moved and placed at different positions within a facility and can be manually moved and placed upon supports proximate to sinks and wash stations, on countertops, on wall mounted stands and supports, on wheeled trolleys which are moved about a facility and the like without limitation. Sounding dispenser 12e illustrates a non-collapsible bottle 50 which carries in an upwardly opening neck 51 a piston pump mechanism 53 which dispenses fluid and includes a suitable sound generator. The sounding dispenser 12f illustrates a similar bottle dispenser, however, provided with a rigid shroud 813 which supports a collapsible bottle 50 therein in a manner as disclosed in U.S. Patent Publication US 2009/0114679, published May 7, 2009 to Ophardt et al, the disclosure of which is incorporated herein by reference.

The sounding dispenser 12g is a wall mounted manually operated dispenser similar to that disclosed in U.S. Pat. No. 8,074,844 to Ophardt et al, issued Dec. 11, 2011, the disclosure of which is incorporated herein by reference but including a sound generator. In sounding dispenser 12g, a bottle 50 is mounted within a housing and adapted to dispense fluid from the top of the bottle with a pump mechanism 53 operated by a manual lever activator 28.

The sounding dispensers 12h and 12i are each a wall mounted dispenser with an inverted fluid containing reservoir 50 from which fluid is dispensed downwardly. Sounding dispenser 12h is manually operated to dispense fluid by a user moving lever actuator 28 as in a manner similar to that disclosed in U.S. Pat. No. 7,367,477 to Ophardt et al, issued May 6, 2008, the disclosure of which is incorporated herein by reference but including a sound generator. Sounding dispenser 12i is a touchless electrical dispenser similar to the dispenser disclosed in U.S. Pat. No. 8,071,933 to Ophardt et al, issued Dec. 6, 2011, the disclosure of which is incorporated herein by reference but including a sound generator.

Sounding dispensers 12j and 12k is each a personal fluid dispenser which is adapted to be carried on the body of a user, for example, a doctor or a nurse within a hospital facility and which can be operated by the user for dispensing hand cleaning fluid. Sounding dispenser 12k is a manually operated dispenser which has no electrical power source and is merely operated manually. Dispenser 12k is preferably similar to the dispenser taught by U.S. Pat. No. 7,984,831 to Kanfer et al, issued Jul. 26, 2011, the disclosure of which is incorporated herein by reference, but modified to include a sound generator. Sounding dispenser 12k is a dispenser with a battery powered electric pump to dispense fluid similar to that disclosed in U.S. Pat. No. 7,898,407 to Hufton et al, issued Mar. 1, 2011, the disclosure of which is incorporated herein by reference, but modified to include a sound generator.

Another sensing dispenser in accordance with the present invention which can be worn and carried by an individual is a dispenser as disclosed in U.S. Pat. No. 5,927,548 to Villaveces, issued Jul. 27, 1999 modified to include a sound generator.

The sounding dispensers 12 preferably comprise manually operated dispensers without any electronic componentry such as sounding dispensers 12e, 12f, 12g, 12h and 12k and without any need for electrical power for operation. However, sounding dispensers which have electrical power such as sounding dispensers 12i and 12j are also useful.

The particular nature of the sound generators 26 to be provided in the sounding dispensers 12 is not limited. Preferred sound generators 26 include air driven whistles, mechanical clickers, and electrically powered speakers of sound chips.

Figure 7:
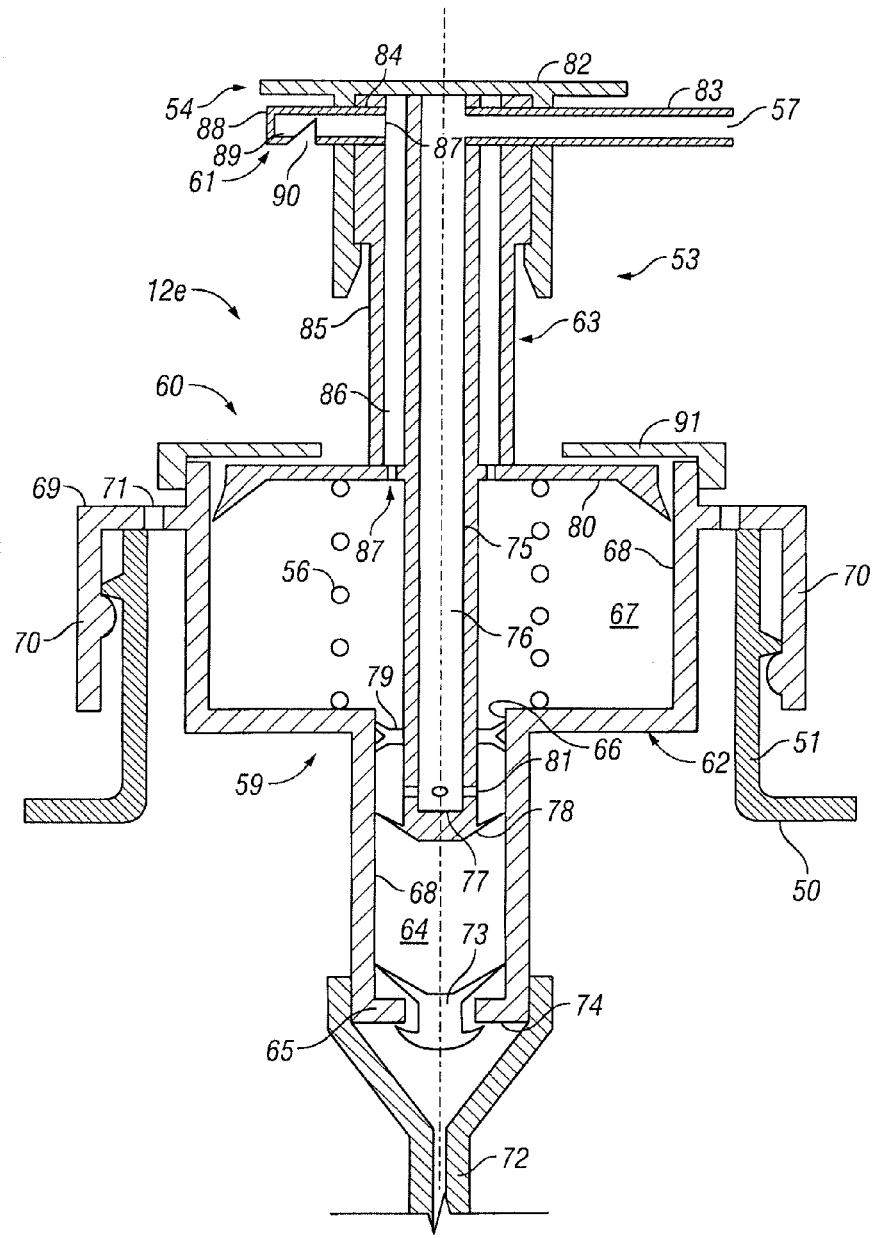
FIG. 7 is a schematic cross-sectional view of a first piston pump assembly for use with the dispenser shown in FIG. 1 including a whistle.

Reference is made to FIG. 7 which schematically illustrates in a schematic partial side view portions of the sounding dispenser 12 in FIGS. 1 and 12e in FIG. 3 in accordance with the present invention. The sounding dispenser 12e has a bottle 50 with an upwardly opening threaded neck 51 about an opening 52. A pump mechanism 53 is provided secured to the bottle 50 engaged about the neck 51 and providing a plunger 54 which, when manually moved downwardly against the bias of a spring 56, discharges fluid from the bottle 50 out of a discharge outlet 57. The sounding dispenser 12e is thus manually operated and is portable and mobile adapted to be supported by a bottom 58 of the bottle 50 being supported on a support surface in a similar manner to that shown with sounding dispenser 12f in FIG. 5. The pump mechanism 53 includes a liquid pump 59 for dispensing the liquid and a sound generator comprising a combination of an air pump 60 and an air whistle 61. Manual movement of the plunger 54 against the bias of the spring 56 compresses air within the air pump 60 and passes air outwardly through the air whistle 61 to generate the sound. Thus, simultaneously with dispensing fluid from the discharge outlet 57, sound is produced by the air whistle 61. The liquid pump 59 has a construction similar to that disclosed in the applicant's U.S. Pat. No. 5,165,577 to Ophardt et al, issued May 20, 1991, the disclosure of which is incorporated herein by reference.

The pump mechanism 53 is formed by a piston chamber-forming body 62 and a piston-forming element 63 coaxially slidable relative to the piston chamber-forming body in a cycle of operation. The piston chamber-forming body 62 is stepped forming an inner liquid chamber 64 having an inner end 65 and an outer end 66 which opens into an enlarged diameter air chamber 67. The liquid chamber 64 and air chamber 67 are formed concentrically within a stepped outer side wall 68. A radially outwardly extending flange 69 extends outwardly from the side wall 68 then axially downwardly as a cylindrical wall 70 which is threaded on its inside as for engagement with threads carried on the neck 51 of the bottle 50. An opening 71 through the annular flange 69 permits unrestricted air flow between the atmosphere and the inside of the bottle 50. The inner end 65 of the liquid chamber 64 has a dip tube 72 secured thereto which dip tube 72 extends downwardly to the bottom of the bottle 50 where the dip tube 72 opens into the bottle providing an inlet for liquid. A one-way valve 73 is provided across an inlet 74 to the liquid chamber 64 to permit fluid flow outwardly therepast but to prevent fluid flow inwardly.

The piston-forming element 63 includes a hollow stem 75 with a central liquid passageway 76 extending from a closed inner end 77 outwardly. Three discs are provided on the piston stem 75, an inner first disc 78, a second disc 79 and a third disc 80. The inner disc 78 extends radially outwardly to engage the inner wall 68 of the liquid chamber 64 and is resiliently deflectable so as to permit fluid flow outwardly therepast yet to prevent fluid flow inwardly therepast. The second disc 79 is located axially outwardly of the inner disc 78 and engages the side wall 68 of the fluid chamber 64 so as to prevent fluid flow either inwardly or outwardly therepast. In between the first disc 78 and the second disc 79 there are provided radially extending inlets 81 through the stem 75 providing fluid flow from between the first disc 78 and the second disc 79 into the liquid passageway 76. The axially outer end of the fluid passageway 76 is closed by a presser cap 82, however, a fluid discharge tube 83 extends radially into the piston-forming element 63 in communication with the liquid passageway 76. With reciprocal movement of the piston-forming element 63 within the piston chamber-forming body 62, fluid from the bottle 50 is drawn up through the dip tube 72 past the one-way valve 73 and is discharged past the inner disc 78 into the liquid passageway 76 to be discharged out the liquid discharge tube 83 and hence out the discharge outlet 57.

The piston-forming element 64 carries the third disc 80 which extends radially outward to engage the side wall 68 of the air chamber 67. Axially outwardly from the third disc 80, the stem 75 is provided with an outer tube 85 coaxially about the stem 75. Between the outer tube 85 and the stem 75, there is provided an annular air chamber 86 closed at an outer end by the presser cap 82. Communication is provided between the air chamber 67 and the annular air chamber 86 via an air portal 87 axially through the third disc 80. An air whistle 61 is provided extending radially from the piston-forming element 63 having an inlet end 87 opening into the annular air chamber 86. The air whistle 61 is shown to extend radially outwardly relative to the piston-forming element 63. The air whistle 61 has resonance tube 84 closed at an outer end 88 and with an axial passageway 89 therethrough opening into the annual air chamber 86. An air splitting triangular notch 90 is positioned on a side of the resonance tube 84 in communication with the passageway 89 so that the passageway 89 is open to the outside through the notch 90. The air pump 60 effectively comprises a stepped pump in which with inward movement of the piston-forming element 63, air is compressed within the air chamber 67 and discharged via the air portal 87 to the annular air chamber 86 and out to atmosphere through the air whistle 61 producing sound. In a return stroke, air enters the air chamber 67 through the air whistle 61 and the air portal 87.

A lid 91 is shown as fixedly secured to the outer end of the piston chamber-forming body 62 at the inner end of the air chamber 67 to prevent the piston-forming element 63 from being withdrawn from the piston chamber-forming body 62. The coil spring 56 is shown disposed axially about the stem 75 between the piston chamber-forming body 62 and the third disc 80 so as to bias the piston-forming element 63 outwardly relative to the piston chamber-forming body 62. In a cycle of operation, with the piston-forming element 63 biased to an outward position as shown in FIG. 7, a user applies axially directed pressure to the presser cap 82 and moves the piston-forming element 63 inwardly. In such movement, fluid from the bottle 50 is dispensed out the discharge outlet 57 onto a user's hand which may be disposed below the outlet 57. Simultaneously, air is discharged through the whistle 61 producing sound. In a return stroke on the piston-forming element 63 being moved from a retracted position to an extended position under the bias of the spring 92, liquid is drawn by the dip tube 72 up into the liquid chamber 64 while air is drawn into the air chamber 67 from atmosphere. A vacuum is not developed within the bottle 50 since air is free to flow via the opening 70 to prevent a vacuum from being produced in the bottle 50.

The pump mechanism 53 illustrated in FIG. 7 is thus adapted for use with bottles which are not to collapse during use. However, such a pump mechanism 53 without the opening 71 may be used with or without the dip tube 72 with collapsible bottles with a vacuum created within the bottle to collapse the bottle with dispensing of fluid. For example, in a sounding dispenser 12*f* shown in FIG. 5, a collapsible bottle 50 may be supported standing in a shroud 813.

Figure 8:
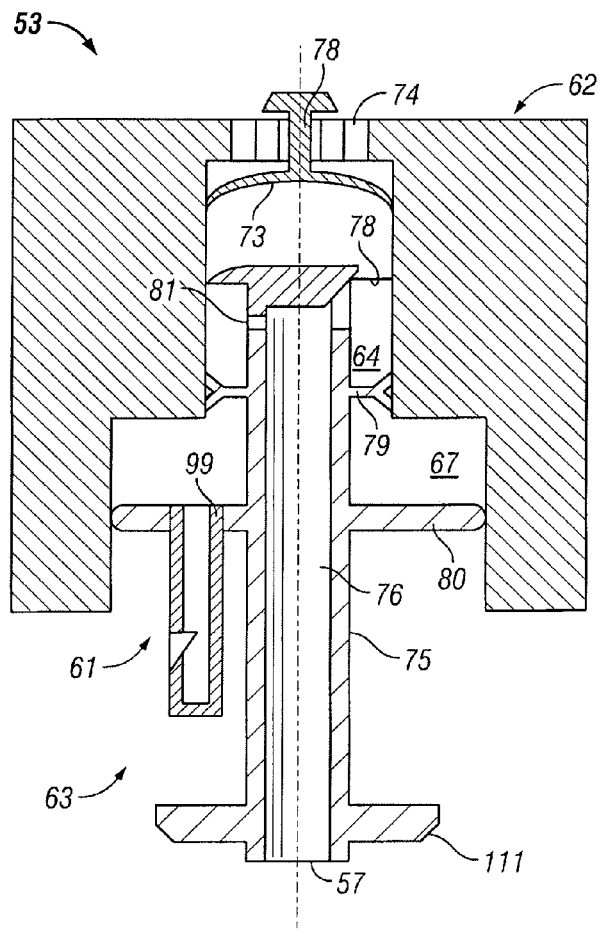
FIG. 8 is a schematic cross-sectional view of a second piston pump assembly for use with one of the dispensers shown in FIG. 3 including a whistle.

Reference is made to FIG. 8 which schematically illustrates a pump mechanism 53 incorporating a liquid pump 59 and a whistle 61 adapted to be engaged to the neck 51 of an inverted bottle 50 for dispensing fluid downwardly as, for example, for use in a sounding dispenser 12*h* or 12*i* in FIG. 6. The pump mechanism 53 in FIG. 8 has a construction analogous in many respects to the construction of the pump in FIG. 7 and similar reference numerals refer to similar elements. The pump mechanism 53 includes an inlet 74 for communication of fluid from inside the bottle 50 to a liquid chamber 64 with a one-way valve 73 permitting flow outwardly but preventing flow inwardly. The piston chamber-forming body 62 forms the liquid chamber 64 and an air chamber 67. The piston-forming element 63 has three discs being an inner first disc 78, a second disc 79 and a third disc 80 with an operation as in the embodiment of FIG. 7 such that moving the piston-forming element 63 inwardly discharges fluid past the inner disc 78 via inlet 81 to a liquid passageway 76 and hence out the discharge outlet 57. In FIG. 8, a whistle 61 is shown as secured to the third disc 80 in an opening 99 in the third disc 80 via which air compressed in the air chamber 67 may be passed outwardly through the whistle 61 to produce sound. The piston-forming element 63 is shown as carrying an engagement flange 112 as is known for coupling of the piston-forming element 63 as to an actuator, not shown.

Figure 9:
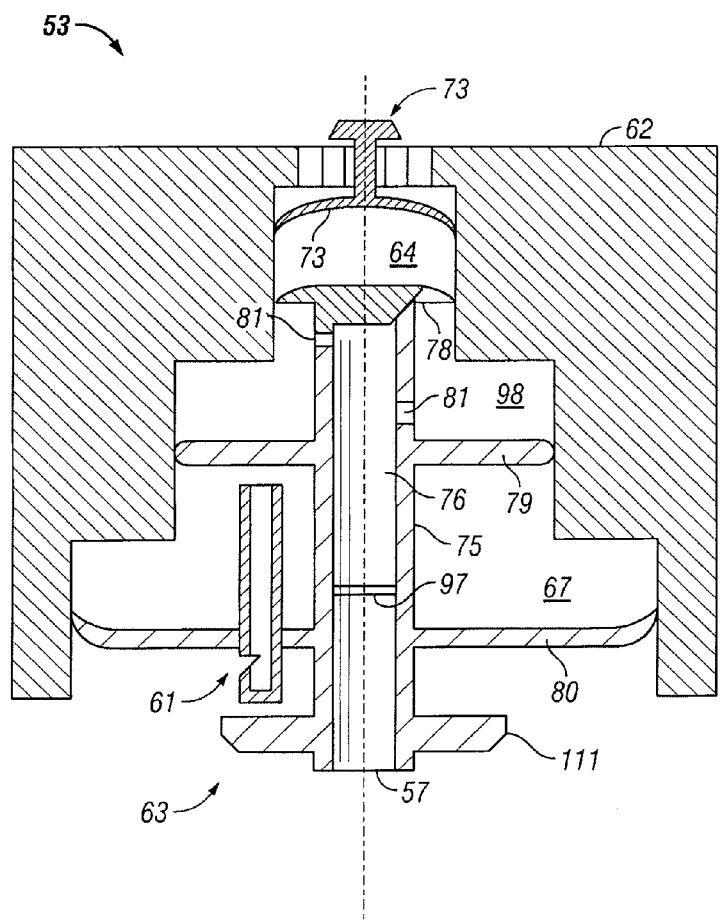
FIG. 9 is a schematic cross-sectional view of a third piston pump assembly for one of the dispensers shown in FIG. 3 including a whistle.
Figures 18, 19:
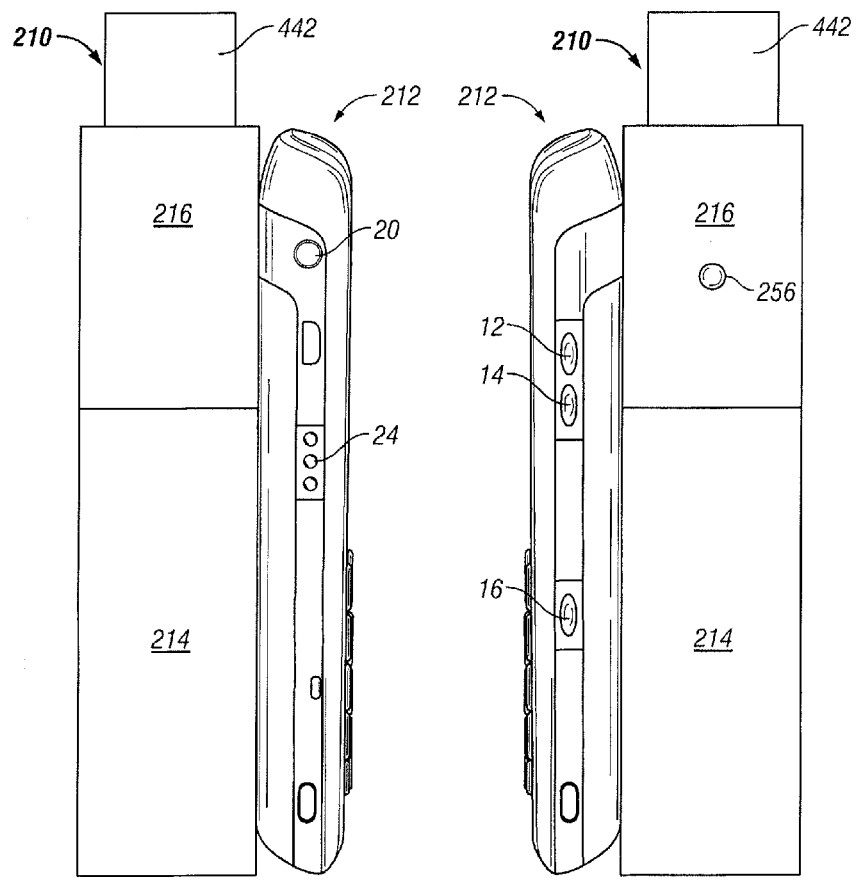
FIG. 18 is a left side view of the dispenser assembly shown in FIG. 16.
FIG. 19 is a right side view of the dispenser assembly shown in FIG. 16

Each of the pump mechanisms illustrated in FIGS. 7 and 8 are adapted for, on one hand, dispensing liquid from a discharge outlet 57 and, on the other hand, dispensing air through an air whistle 61 to produce sound. Reference is made to FIG. 9 which shows a pump mechanism 53 adapted to discharge foam from a discharge outlet 57 and air through the air whistle 61. The pump mechanism 53 shown in FIG. 9 is similar to a pump illustrated in U.S. Pat. No. 7,708,166 to Ophardt, issued May 4, 2010, the disclosure of which is incorporated herein by reference. The pump mechanism 53 in FIG. 9 dispenses liquid mixed with air from the discharge outlet 57 as taught by U.S. Pat. No. 7,708,166 and has in addition an additional air chamber 67 and a third disc 80 provided for discharging air through an air whistle 61. In FIG. 9, three chambers are provided shown as a first chamber 64, a second chamber 98 and a third air chamber 67. The piston-forming element 63 carries three discs, a first inner disc 78, a second disc 79 and a third disc 80. In a known manner as illustrated in FIG. 18 of U.S. Pat. No. 7,708,166, liquid from the bottle 50 and air from the atmosphere is mixed in the second chamber 98 and discharged via the inlet 81 to the stem passageway 76 passing through a foam generator 97 disposed within the stem passageway 76. The first disc 78 and second disc 79 effectively form a stepped pump for discharge of liquid mixed with air as foam. The third disc 80 is disposed in the air chamber 67 forming a stepped air pump which discharges air out the whistle 61 in the same manner illustrated in FIG. 8.

Various pumps are known which are adapted to dispense foam and provide a liquid pump for dispensing liquid and an air pump for dispensing air with the liquid and air to be mixed and generate foam. In accordance with the present invention, such foaming pumps may be modified so as to provide pumps which produce sound by directing some or all of the air from the air pump through a sound producing generator. For example, the sounding dispenser 12*h* illustrated in FIG. 5 may comprise a hand-held dispenser for personal use as disclosed in U.S. Pat. No. 7,984,831 which includes both a liquid pump and an air pump and in which some or all of the air from the air pump can be directed through a sound producing mechanism such as a whistle.

As to the particular nature of the whistle 61, many different types of whistles may be used as known in the art. For example, ultrasonic whistles may be provided as taught in U.S. Pat. No. 6,698,377 to Topman et al, issued Mar. 2, 2004. Another example of an air whistle construction which could be modified for use in accordance with the present invention is disclosed in U.S. Pat. No. 5,816,186 to Shepherd, issued Oct. 6, 1998. The whistles 61 in the preferred embodiments have been shown as separate whistle inserts secured to components of the pump as, for example, to extend axially or radially. The nature of the air whistle is not limited and while whistles with resonating chambers have been shown, various other devices can be utilized which produce sound by the passage of air such as vibrating reeds. While the preferred embodiments show sound creation by passing air through a whistle with the air being air pressurized in an air pump that the passing air can also be provided by creating a vacuum in a pump and by drawing air in through a sound producing device such as a whistle.

Figure 10:
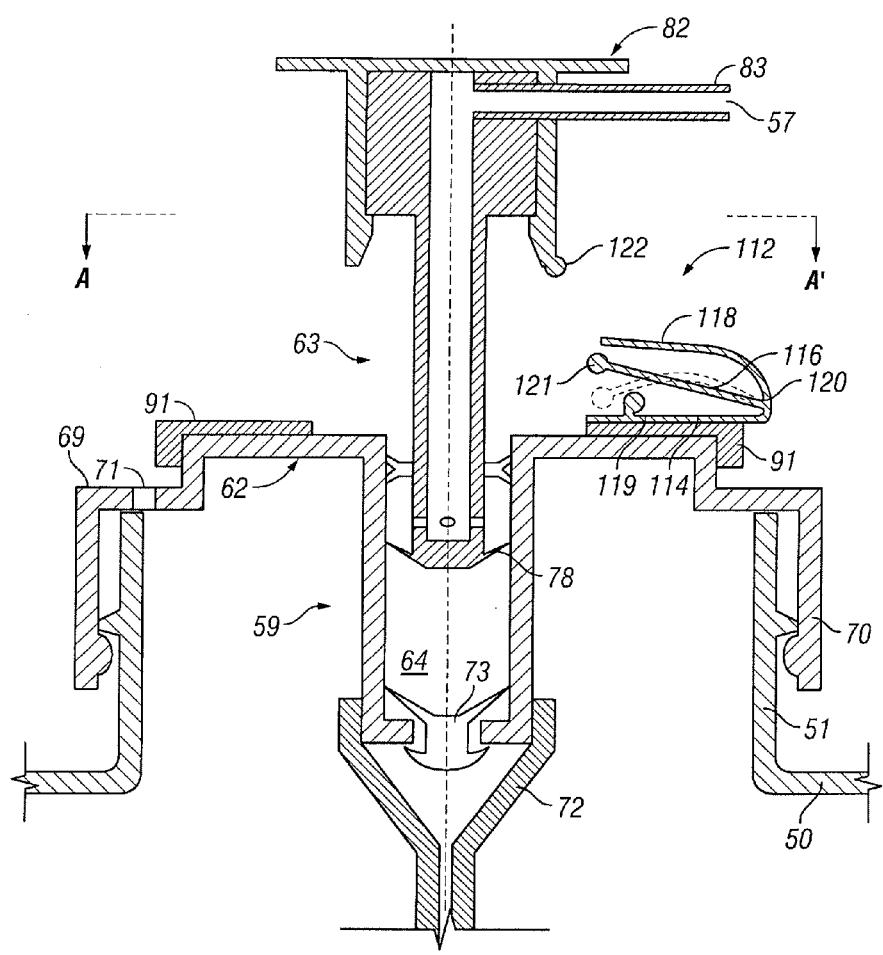
FIG. 10 is a schematic cross-sectional view of a fourth piston pump assembly for use with the dispenser shown in FIG. 1 including a sound producing clicker mechanism.
Figure 11:
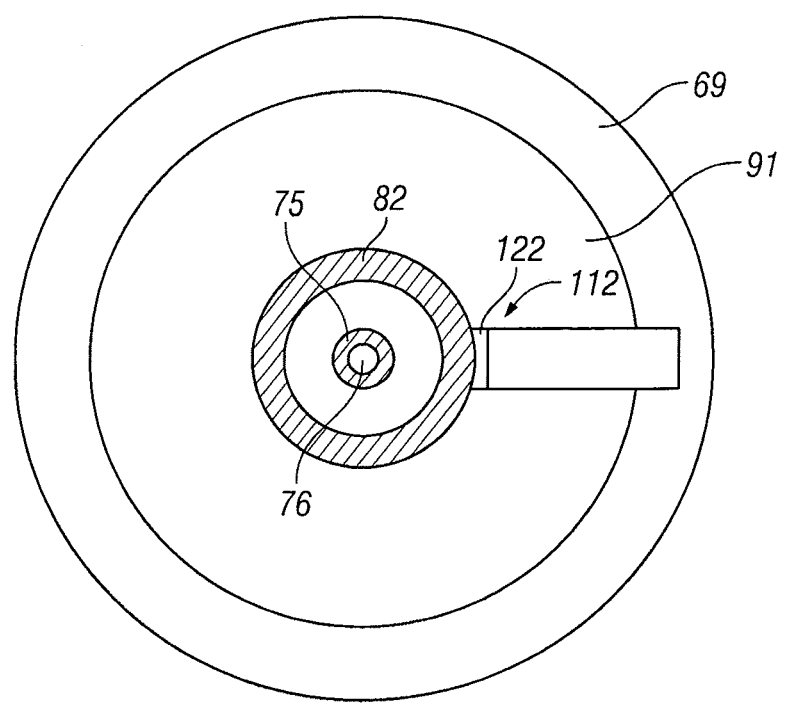
FIG. 11 is a schematic cross-sectional view along section line A-A' in FIG. 10.

Reference is made to FIGS. 10 and 11 which illustrate a pump mechanism which is similar to the pump illustrated in FIG. 7 in having an essentially identical liquid pump 59 but in which the air chamber 60 and whistle 61 of FIG. 7 are eliminated and a sound generator is provided in the form of a clicker mechanism analogous to the clicker mechanism disclosed in U.S. Pat. No. 3,538,637 to Smith, issued Nov. 10, 1970, the disclosure of which is incorporated herein by reference. As seen in FIG. 10, the presser cap 82 is adapted to be manually moved downwardly to dispense fluid from the bottle 50 out the discharge outlet 57. For ease of illustration, a spring to bias the piston-forming element 63 outwardly is not shown. Mounted to one side of the lid 91 as best seen in top view in FIG. 10 is a sound generator in the form of a clicker mechanism 112 which extends radially and includes a base 114, a flexible reed 116, a sound arm 118 and a stop member 119. The flexible reed 116 is fixedly secured at one end 120 to the base 114 and extends to a freely suspended distal end 121 which is in the shape of a cylinder. The presser cap 82 carries at its lower end a similar contact cam 122 also in the shape of a cylinder parallel to the cylinder on the distal end 121 of the reed 116. The stop member 119 is fixed to the base 114 and has a distal end in the shape of a cylinder parallel the cylinder of distal end 121. On movement of the presser cap 82 downwardly, the contact cam 122 engages the distal end 121 of the reed 116 deflecting the reed 116 to move it downwardly with the reed 116 to become deflected and engaged about the stop member 119 and to be biased to a lower position illustrated in dashed lines in FIG. 9 in which the contact cam 122 of the presser cap 82 may move downwardly past the reed 116 at which time the reed 116 due to its inherent resiliency will snap upwardly into engagement with the sound arm 118 snapping against the sound arm 118 to make a clicking noise. The clicker 112 may be configured such that on return of the contact cam 122 of the presser cap 82 upwardly past the reed 116, a second clicking noise is created although this is not necessary.

While the embodiment of FIGS. 9 and 10 illustrates one mechanism of producing a clicking sound with a mechanical clicker arrangement on movement of a piston pump axially in a cycle of operation, various other mechanical clicker devices may be used. For example, clicker devices of the type illustrated in U.S. Pat. No. 724,545 to Conklin, issued Apr. 7, 1903 or the type illustrated in U.S. Pat. No. 8,033,201 to Cutler, issued Oct. 11, 2011 may be adapted or incorporated in various different configurations. For example, as the sounding dispenser 12k illustrated on FIG. 5, a hand-held dispenser as disclosed in U.S. Pat. No. 7,984,831 could be incorporated so as to adopt a clicker mechanism as a sound generator providing a sound on manual movement of a pump actuator and maintain that dispenser as useful, for example, for dispensing fluid and air mixed as foam.

As another form of a sound generator for use in the present invention, the sound generator may comprise an electrically driven electronic sound producing element or a speaker. For example, in sounding dispensers illustrated as 12i and 12j in FIG. 6 which have a source of electrical power, the electrical power may be used to generate sound when the dispenser is activated or fluid dispensed. The sound generator 26 thus could be a simple electrically powered speaker or digital sound chip such as a piezoelectric transducer. Thus, for example, in electrically powered dispensers, such a sounding dispenser as 12i or 12j shown in FIG. 6, on activating the dispenser to dispense fluid, the electrically powered sound generator may be activated to produce sound.

The sound generator 26 and the sound sensor 32 as shown, for example, in FIG. 2, are adapted to be compatible such that the sound sensor 32 will sense sound generated by the sound generator 26. Preferably, the sound produced by the sound generator 26 is at selected frequencies so as to be readily discernible and distinguishable from sound generated within the working environment. The sound generator may be selected to have a particular profile which can assist the sound sensor 32 in recognizing the sound as emanating from a sounding dispenser 12. For example, the sound 30 which is produced may have a variance in amplitude or frequency which can be characteristic of a signature for particular sounding dispensers. For example, an air whistle 61 may have a particular sound characteristic over time which can be recognized by the sound sensor 32 to distinguish the sound 30 from the whistle 61 from ambient sounds. Additionally, the whistle 61 may be adapted to produce sound in both an inward stroke and an outward stroke of movement of a piston which can be recognized by the sound sensor 32 and assist in distinguishing over sounds in the environment. Similarly, the sound 30 from a clicker mechanism such as shown in FIGS. 9 and 10 may click both on an instroke and an outstroke to assist in distinguishing a sound made from the clicker from sound in the environment. Similarly, insofar as sound is produced electronically in a sounding dispenser, the sound produced electronically may have a particular profile of frequency, or amplitude over time or emit a number of sounds.

In developing suitable air whistles along the lines of those disclosed in FIGS. 7 to 9, the timing and manner in which the air can be delivered to an air whistle can be selected so as to provide for advantageous operation of the air whistle. For example, insofar as pressurized air is desired to be delivered from an air chamber 67 to the whistle 61, a time delay valving arrangement may be provided between the air chamber 67 and the whistle 61 so as to not open until air within the air chamber 67 has reached a certain pressure and then on reaching that pressure, the air is then permitted to discharge through the air whistle resulting in a higher velocity discharge of air through the air whistle. The pressurizing of air and the ease of passage of air from atmosphere to flow back through the whistle into the air chamber can be accommodated by various valving mechanisms and, amongst other things, avoid a significant increase in the pressures required to move the piston-forming element 63.

Each of the illustrated pump mechanisms in FIGS. 7 to 10 show piston pump mechanisms, however, any manner of pump mechanisms may be used to dispense fluid and, if desired, to pass air through a whistle.

In the preferred embodiments illustrated, as seen in FIG. 1, the sound sensing mechanism 14 is shown to communicate wirelessly with a wireless router 16 and the wireless router 16 is shown to communicate with the Internet 18 via which there is communication with the computing system 20. However, such communication from the sound sensing mechanism 14 need not be wireless. For example, while not believed to be preferred, the sound sensing mechanism 14 could be hardwired to a router or to the Internet or to the computing system 20. Similarly, wireless routers 16 are preferably wireless routers for communication as through a local area network or wide area network with the Internet 18, however, non-wireless routers could be substituted which such routers being hardwired as to the Internet 18 or to the computing system 20. Preferably, the sound sensing mechanism 14 for convenience and easy location of a plurality of sound sensing mechanisms 14 within a facility, communicates wirelessly to a router 16 or to the Internet 18 or to the computing system 20, however, while it is preferred that wireless routers 16 are used, the manner of receiving signals from the sound sensing mechanisms 14 and providing them to the computing system 20 is not limited to being through routers or the Internet or to being wired and may be hardwired. For example, in FIG. 1, arrow 113 indicates that a sound mechanism 14 could communicate directly with the Internet or the computing system 20. The communication between the sound sensing mechanism 14 may be one way for transmission of data to the computing system 20 or could be two way as, for example, to run diagnostic checks on the sound sensing mechanism or to request and retrieve information from the sound sensing mechanism 14 or to confirm safe data receipt. The controller 34 of the sound sensing mechanism 14 may include data storage capabilities to store data for some time and deliver the data in packets to the computing system.

The computing system 20 has been schematically illustrated in FIG. 1 as but a single user at a single computer. However, the computing system 20 may, as is well known in the art, comprise various structures such as preferably a system with data producing modules which may comprise a web tier of servers that communicate with a data tier of servers. A web tier of servers could deliver information through web pages, receive user information to be processed, provide web service for multiplexer use and for reporting to facility managers, to generate alerts and notification. A data tier server can provide central data storage. The computing system may include a facility manager such as an individual person at a computer. The facility manager preferably is able to communicate with the data producing web tier and the data tier as by the Internet. The facility manager preferably has the capability of reviewing reports and managing all master data. Preferably, the computer has the capability of communicating with a facility database which may include various information from a facility such as, for example, in the case of a hospital, data regarding operations, occupancy, disease and infection incidence, and the like. Thus, in accordance with the present invention, data gathered regarding the usage of fluid dispensers at a facility or different areas within a facility can be correlated, as for example, to occupancy of the facility or different parts of a facility to measure the relative use of hand cleaning sounding dispensers within the facility.

The invention provides not only an apparatus for monitoring of dispensers but also a method of monitoring dispensers comprising a method of compliance monitoring of hand washing within a facility comprising producing a sound each time a dispenser is activate, remotely monitoring the sounds produced by one or more sound sensors positioned to receive sounds and transmitting data representative of the sounds sensed by the sound sensors to a central computer.

Figure 12:
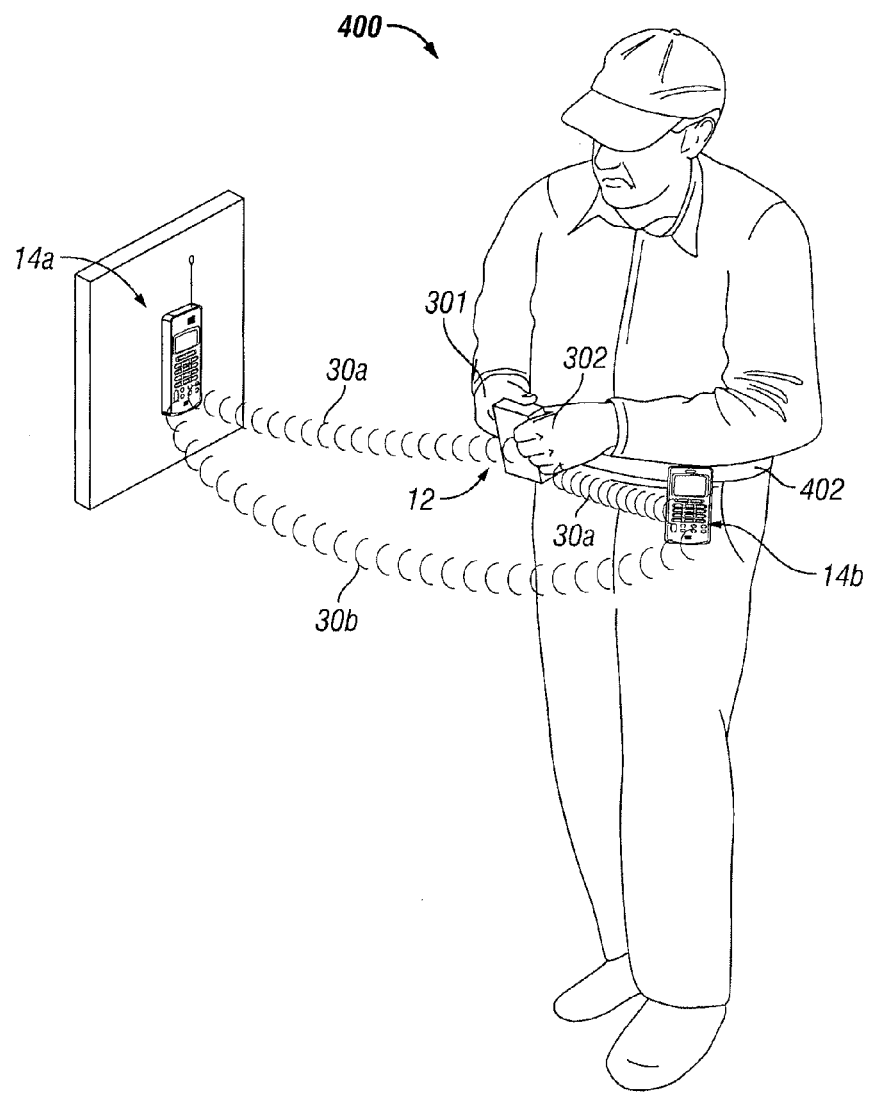
FIG. 12 is a front pictorial view of a person carrying a personal compliance sounding dispenser in accordance with a third embodiment of the present invention.

Reference is made to FIG. 12 which illustrates a person 400 wearing a belt 402 upon which there is removably carried a personal fluid sounding dispenser 12. The sounding dispenser 12 is shown in pictorial view in FIG. 13, in cross-sectional views along section lines B-B' in FIG. 14 and along section line C-C' in FIG. 15.

Figure 14:
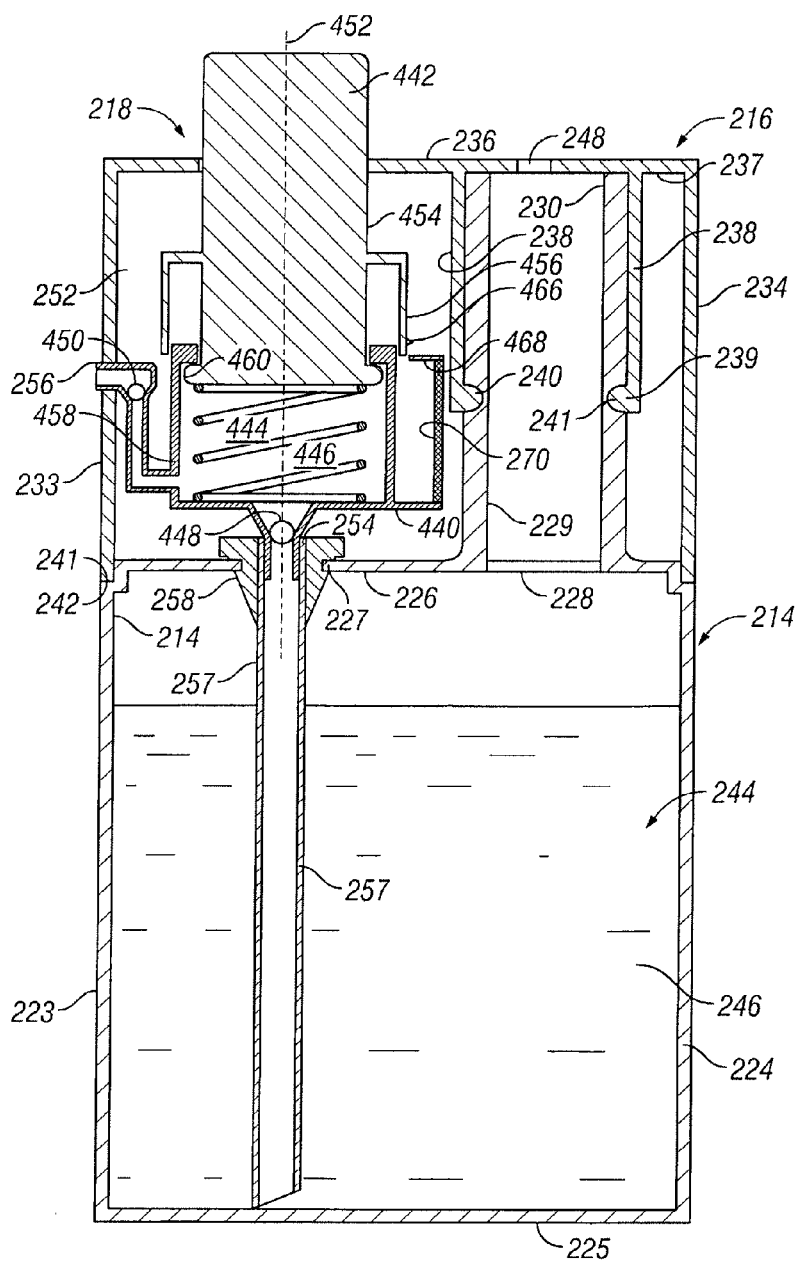
FIG. 14 is a vertical cross-sectional rear view along section line B-B' in FIG. 13.

As best seen in FIG. 14, the sounding dispenser 12 includes a reservoir 214, a top cover 216 and a pump 218.

Figure 13:
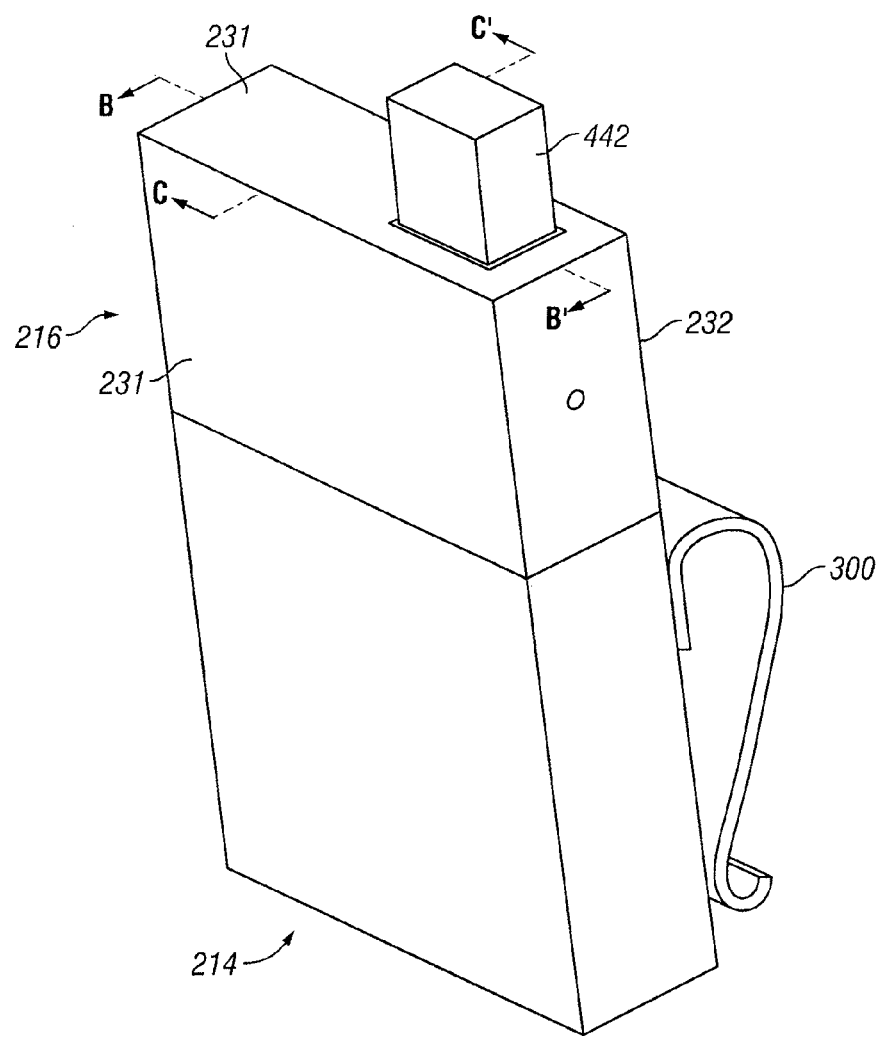
FIG. 13 is a front pictorial view of the personal compliance sounding dispenser of FIG. 12.

The reservoir 214 is shown as generally rectangular having a front 221, a back 222, a left side 223, a right side 224, a bottom 225 and a top 226. The reservoir 214 is enclosed but for two openings provided through the top 226 namely a pump opening 227 and a filler opening 228. The filler opening 228 is within an upstanding tube 229 open at an upper end 230. The reservoir 214 defines an enclosed internal space 244 to receive a fluid 246 to be dispensed. As seen in FIG. 13 only, the reservoir has an optional resilient clip member 300 on its rear for removably engaging clothing of the person such as by engaging the person's belt. The reservoir 214 may be refillable or alternately could be a single use reservoir to be replaced and discarded after the reservoir may be empty.

The cover 216 is also generally rectangular in shape having a front 231, a back 232, a left side 233, a right side 234 and a top 236. The cover 216 is open at its bottom such that interior of the cover 16 there is provided a compartment 252.

Figure 15:
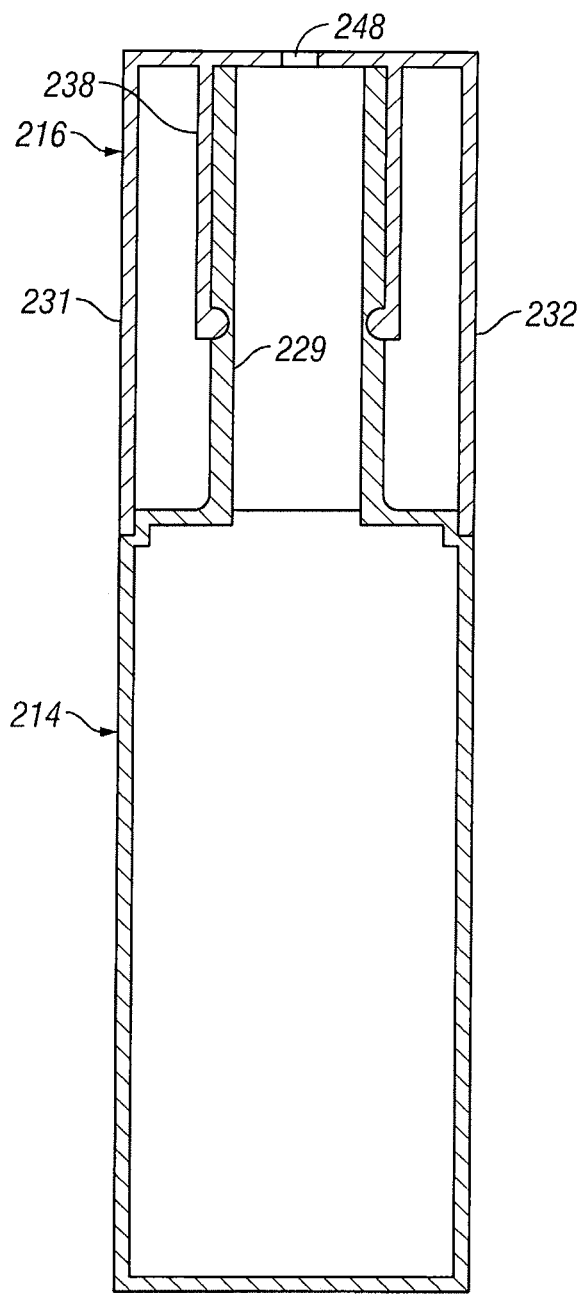
FIG. 15 is a vertical cross-sectional rear view along section line C-C' in FIG. 13.

From an inside surface 237 of the top 236 of the cover 216, a tubular member 238 extends downwardly to a lower end 239. The lower end carries an annular inwardly extending boss 240. The boss 240 is complimentary to an annular groove 241 extending circumferentially about the tube 229 on the reservoir. The tubular member 238 is sized to be coaxially slidably disposed snug about the tube 229 of the reservoir 214 with the boss 240 engaged in snap fit in the groove 241 forming a fluid impermeable seal therewith and to snap fit the cover 216 onto the reservoir 214 to resist upward removal. As seen in FIGS. 14 and 15, the reservoir 214 carries a ledge 242 which extends circumferentially about the top 226. A lower edge 241 of each of the front 231, back 232 and two sides 233 and 234 of the cover 216 are received in the annular ledge 242 about the reservoir 214 so as to prevent relative rotation of the cover 216 relative to the reservoir 214 about the tube 229.

The top 236 of the cover 216 has an air vent opening 248 therethrough open into the tube 229 to provide an entrance for air into the reservoir space 244 such that when fluid 246 is dispensed from the reservoir by the pump 218, air may enter the reservoir to avoid build up of a vacuum within the reservoir space 244. A vent plug, not shown, may be provided for manual movement between opened and closed position to sealably close the air vent opening 248. The pump 218 is removably located within the compartment 252 within the cover 216.

The pump 218 is a manually operated pump 218 schematically illustrated as comprising a piston pump having a piston chamber-forming body 440 within which a piston 442 is axially slidable and biased to an outer position as by a spring 444. The piston extends outwardly beyond the top 236 of the cover 216 for engagement by the user. On a user depressing the piston 442 against the bias of the spring 444, fluid is dispensed out a fluid outlet tube 256. Between a dip tube 257 and a fluid chamber 446 formed within the pump, there is an inlet one-way valve 448 which permits flow outwardly from the reservoir 214 through an inlet tube 254 into the chamber in the pump. As well, there is a one-way outlet valve 450 providing output from the chamber 446 to the outlet tube 256 merely outwardly from the chamber.

The cover 216 preferably securely carries the pump 218 with the dip tube 257 and a grommet 258 secured thereto to form a unit which can be in a snap fit manner coupled and removed from engagement with the reservoir 214.

The pump 218 is secured within the compartment 252 of the cover 216 with the pump outlet tube 256 extending through the right side 233 of the cover 216. While not shown, a manually operated discharge outlet plug may optionally be provided for manual manipulation between open and closed positions to open and sealably close the outlet tube 256.

The piston 442 has a piston head 460 which is sealably engaged within the piston chamber-forming body 440 and each is cylindrical and coaxial about a central axis 452. The piston 442 is shown as carrying a cylindrical inner wall 454 and a cylindrical outer wall 456. The body 440 has a cylindrical wall 458 with a catch shoulder to engage on a catch shoulder on the piston head 460 to stop the piston from being slid axially fully out of the piston chamber-forming body. After the piston 442 has been depressed by a user, on release the spring 444 urges the piston outwardly and draws fluid from the reservoir 214 into the chamber 446.

A shoulder 466 is carried on the outer wall 456 of the piston is adapted to engage a sound producing deflectable reed 468 carried on a member 270 secured to the piston chamber-forming body 440. On the piston moving in a stroke of operation, the shoulder 466 engages the reed 468 such that the reed 468 is deflected to produce a sound 30b shown on FIG. 12.

As seen on FIG. 12, this sound 30b is to be sensed by a suitable sound sensing mechanism 14 which may be separate from the person as, for example, if the person is within an array of sound sensing mechanisms 14 in a health care facility 100 as seen in FIG. 5. One such sound sensing mechanism 14a is illustrated in FIG. 12 as a notional wall to receive sound 30a from the sounding dispenser 12.

However, a preferred arrangement as seen in FIG. 12 is to provide a sound sensing mechanism 14 on the person. In this regard, FIG. 12 shows a sound sensing mechanism 14b also carried by the person 400 by being removably coupled to the person's belt 402. The sound sensing mechanism 14b in FIG. 12 preferably is a portable hand held pocket-size personal computer such as preferably a smart phone 14b which includes a microphone to sense the sound 30a from the sounding dispenser 12. The personal computer or smart phone 14b can suitably communicate data regarding the operation of the sounding dispenser 12. This communication by the smart phone can be by various methods including wirelessly by Wi-Fi or Bluetooth signals to one of the routers 16 as is within the normal expected capacity of the smart phone, with the smart phone, for example, submitting the information immediately on dispensing of fluid or collecting and storing information for transmission periodically. The smart phone can also communicate the information as sound 30b using a speaker system within the smart phone to generate a sound 30b to be sensed by the remote sound sensing mechanism 14a. The sound 30a generated by the personal fluid sounding dispenser 12 preferably is a sound which is distinguishable from the sound 30b generated by the cell phone. Since the sound 30a need only travel a short distance from one location carried on the person to another location carried on the person, the magnitude of the sound 30a may be relatively small compared to the magnitude of the sound 30b to travel in a facility from the person 300 to a nearest facility mounted sound sensing mechanism 14a. As the magnitude of the sound 30a can be much smaller, the use of sounds which are audible is less offensive and problematic. Use of a relatively small clicking sound as the sound 30a is adequate.

Many known smart phones have pre-existing capacities to listen for and recognize sounds as well as to generate various sounds. Programming of smart phones to act in a manner as desired to recognize sounds 30a in a microphone and generate a sound 30b on their speaker system can be a simple matter which does not need customized programming although a simple downloadable application preferably can be provided.

FIG. 12 shows the sounding dispenser 12 operated by the person 300 with one hand 301 to dispense fluid onto the other hand 302 while the dispenser is coupled to the person's belt. The sounding dispenser 12 may be disengaged from the person's body and, for example, placed on a flat surface as a tabletop and may be used to dispense the fluid from the discharge tube 256 as onto a user's hand. Alternatively, a sounding dispenser 12 may be held in one of a person's hands and activated to dispense fluid, for example, onto the other of a person's hand or an object.

Preferably, the fluid 246 within the reservoir 214 is a relatively low viscosity disinfecting or cleaning fluid such as alcohol or an alcohol and water based fluid.

The pocket-sized personal computer is preferably selected from commercially available devices such as smart phones, personal digital assistants (PDA) and pocket personal computer (Pocket PC). A preferred example of suitable commercially available smart phones include BLACKBERRY (trade mark) smart phones and Apple IPHONE (trade mark) smart phones. One example of one suitable commercially available PDA is the APPLE I-POD (trade mark) with WI-FI enablement. An example of a suitable commercially available PDA and Pocket PC is represented by the products sold by Hewlett Packard under the trade marks HP iPAQ (trade mark).

Reference is made to FIGS. 16 to 19 showing a personal dispenser assembly 210 in accordance with another embodiment of the present invention and comprising in combination a communication enabled, portable handheld pocket-sized, personal computer 212 and a sounding dispenser 14 identical to that shown in FIGS. 12 to 15. The pocket-sized, personal computer 212 illustrated is a BLACKBERRY 9700 brand smart phone 212 sold under this trade-mark name by Research In Motion Inc. and having, as is known, a main computer housing or casing 300 carrying on its front 301a display screen 302, a keypad of keys 304, a microphone and speaker 306, carrying on its top a lock key 308 and a mute key 310, carrying on its right side volume keys 312 and 314 and a programmable convenience key 316 typically used to operate a camera 318 seen in FIG. 17 and, carrying on its left side, a headset jack 320, a mini USB port 322 and a convenience key 324 which can be programmed but is typically used to operate voice commands.

The smart phone 312 carries on its rear 326 a battery cover 328 which removably couples with the main casing 300 by sliding upwardly for insertion and downwardly for removal.

Figure 16:
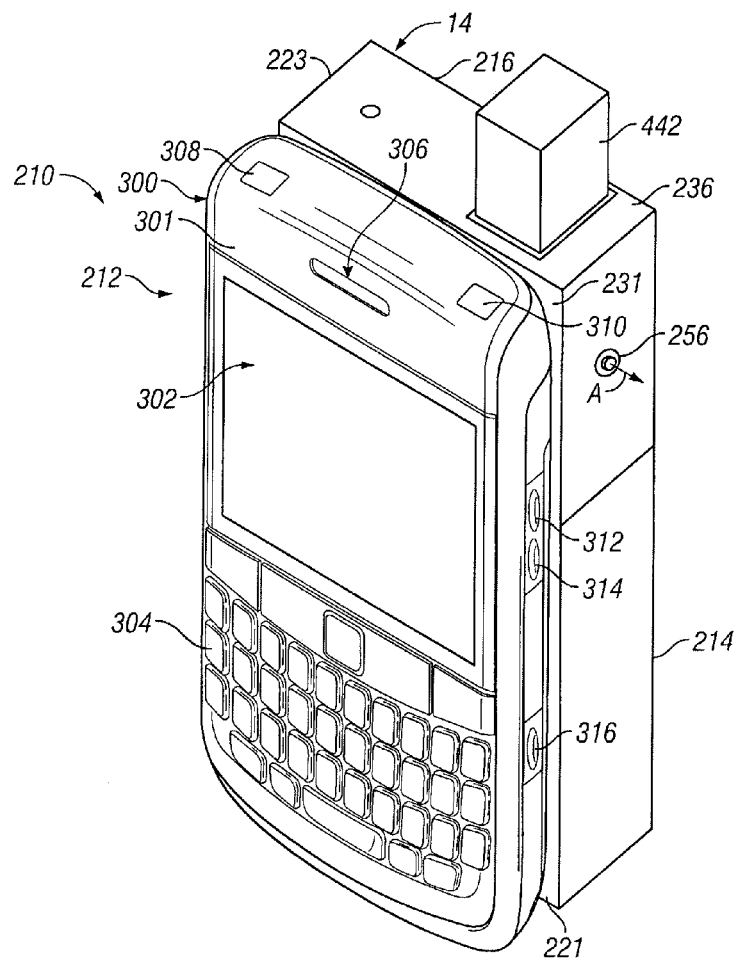
FIG. 16 is a front pictorial view of a personal compliance dispenser assembly in accordance with a fourth embodiment of the present invention.
Figure 17:
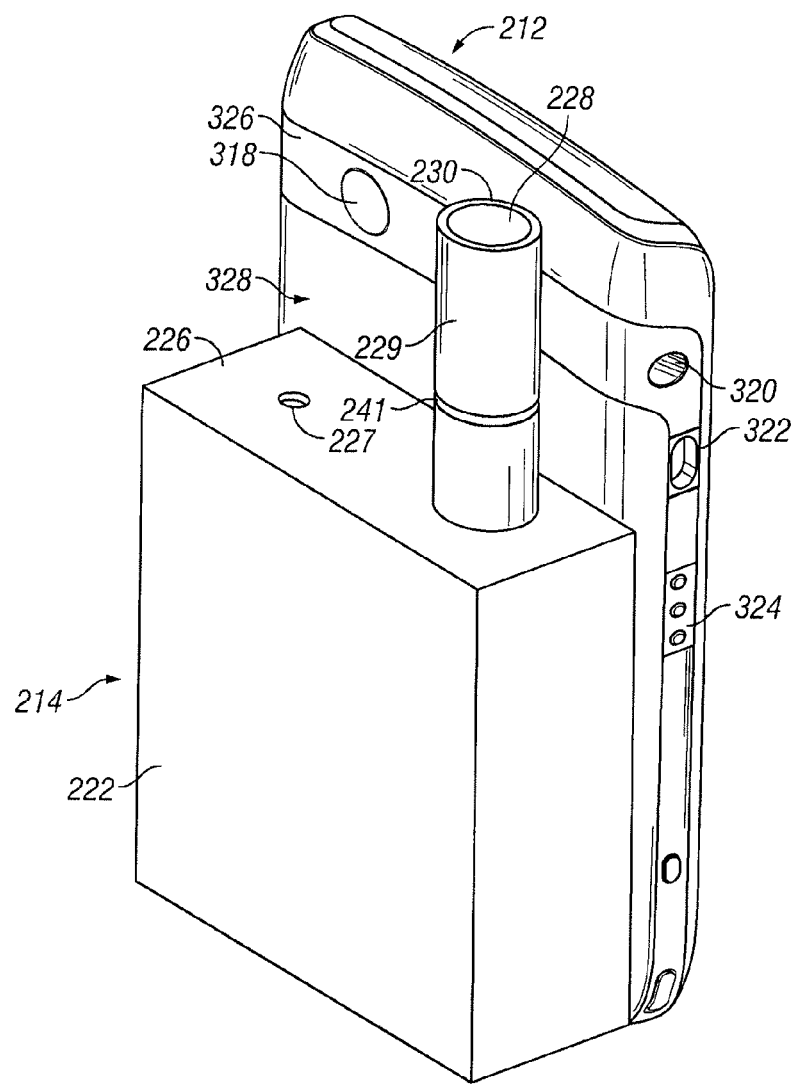
FIG. 17 is a rear pictorial view of the dispenser assembly shown in FIG. 16 however, with a top cover and an associated pump mechanism removed.

In the embodiment of FIG. 16, sounds 30b are, as was the case with the embodiment of FIGS. 12 to 15, generated by the reed 468 on operation of the manual pump, however, in the embodiment of FIG. 16, the sounds are directed through the dispenser 12 directly to the smart phone 212 facilitating the smart phone 212 in sensing the sound 30b with its microphone 306. Preferably, as seen in FIG. 4, the member 270 carrying the reed 468 is physically connected to the main casing 300 of the smart phone 212 to assist in transfer of sound. For example, the reservoir 214 is physically secured to the battery cover 328 preferably with the reservoir 214 including the battery cover 322 integrally molded as one element.

Figure 20:
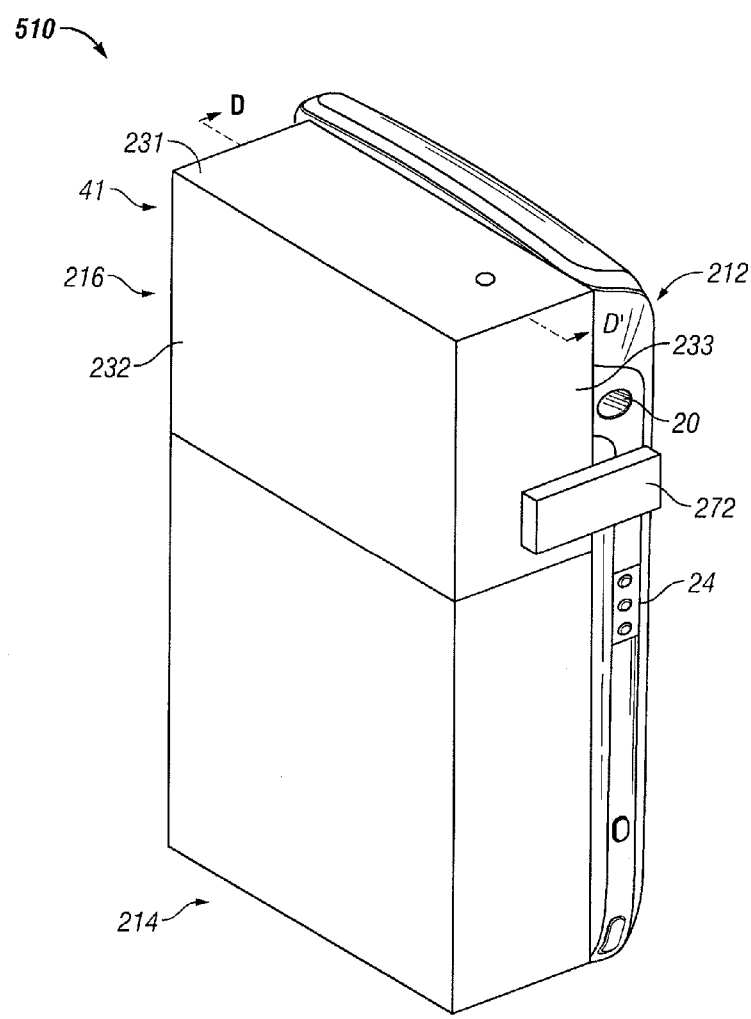
FIG. 20 is a rear pictorial view of a personal compliance dispenser assembly in accordance with a fifth embodiment of the present invention.
Figure 21:
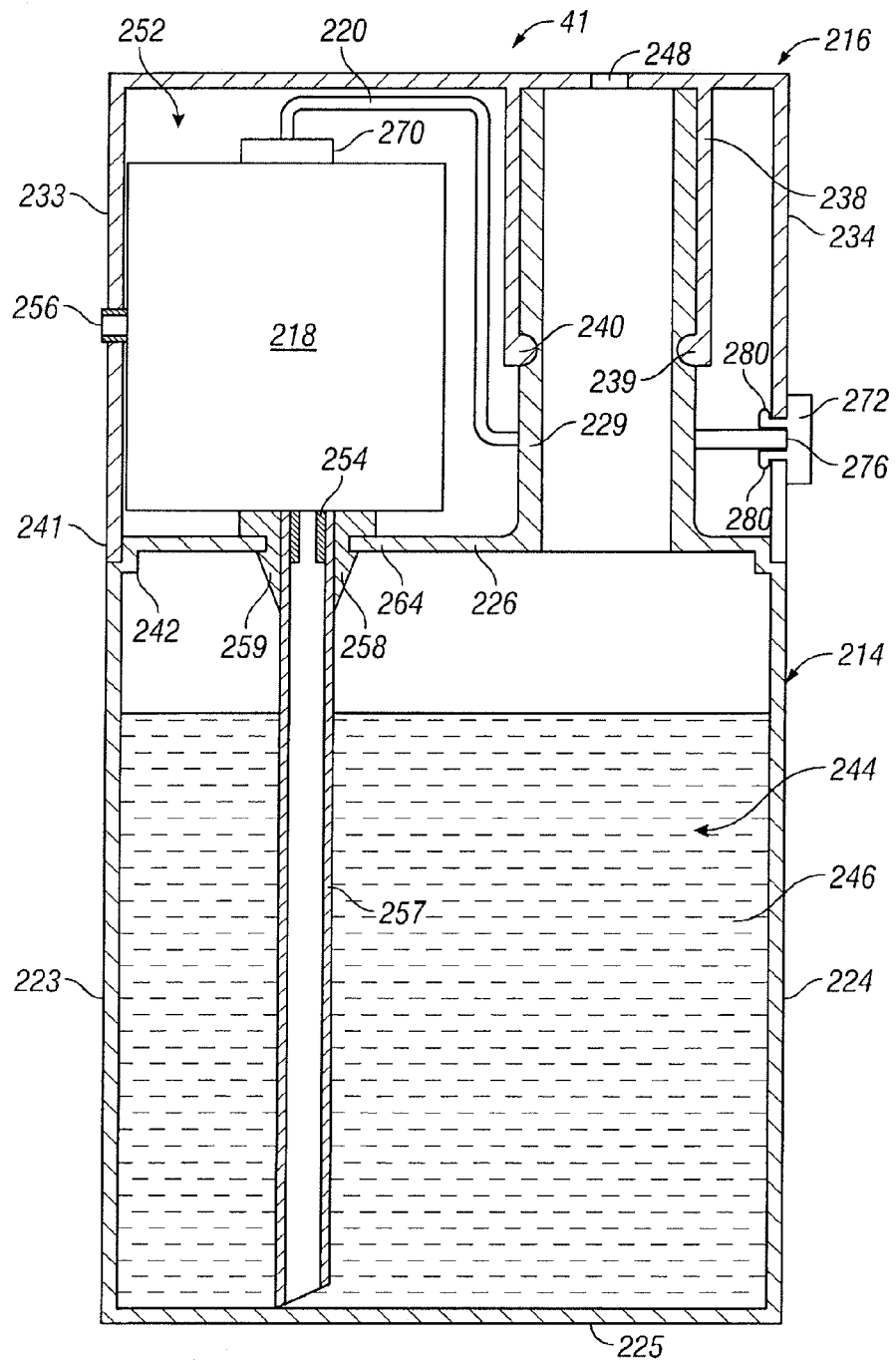
FIG. 21 is a vertical cross-sectional rear view along section line D-D' in FIG. 20.

Reference is made to FIGS. 20 to 23 showing a personal dispenser assembly 310 in accordance with another embodiment of the present invention and comprising in combination a communication enabled, portable handheld pocket-sized, personal computer 212 and a non-sounding dispenser 41 having similarities to the sounding dispenser used in of FIGS. 16 to 19. The non-sounding dispenser 14 in FIGS. 20 to 23 is identical to the sounding dispenser 12 in FIGS. 12 to 19 with the notable exception that its pump 218 is not a manually operated pump but rather an electrically powered pump and thus the piston 442 seen in FIG. 16 is not found in FIG. 20. In the embodiment of FIG. 20 the electrically powered pump 218 shown in FIG. 21 is electrically connected to the smart phone by a patch cord 220 including an external male phone connector 272 as seen in FIG. 20.

Figure 22:
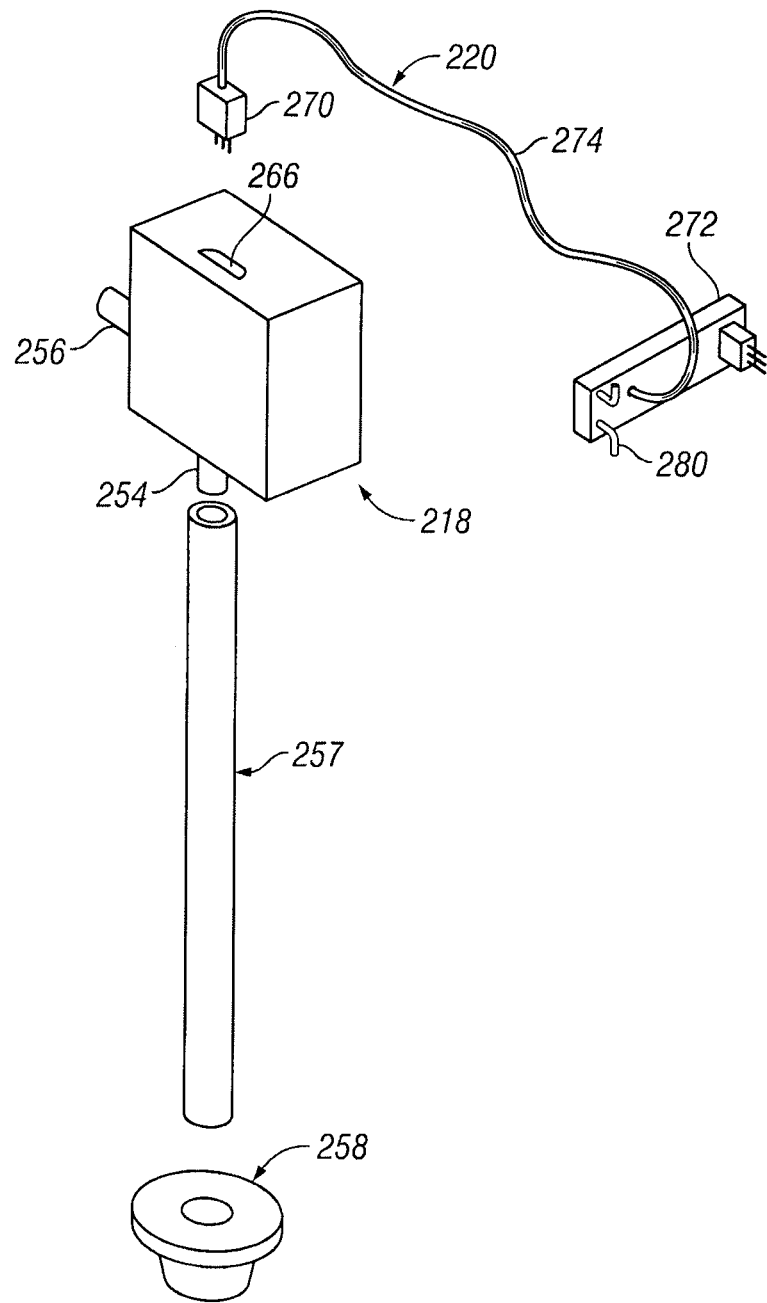
FIG. 22 is a schematic exploded pictorial view of the pump and patch cord of FIG. 21.

The electrically powered pump 218 is schematically shown in FIGS. 21 and 22 and preferably is a piezoelectric diaphragm micro pump having an inlet tube 254 and an outlet tube 256. The inlet tube 254 has a dip tube 257 sealably engaged coaxially thereabout. As was the case with the manually operated pump, a resilient stopper member 258 coaxially overlies the dip tube 257. The resilient stopper 258 carries an annular slotway 259 thereabout sized to receive the circumferential edge 264 of the pump opening 227 therein so as to removably sealably couple the pump 218 to the reservoir 214 in a sealed friction fit relation. The dip tube 257 extends downwardly inside the reservoir 214 to proximate the bottom 225 of the reservoir 214.

As seen in FIG. 22, the pump 218 has a female mini USB port 266.

The patch cord 220 comprises an elongate flexible wire 274 comprising a grouping of insulated electrical conductors. The patch cord 220 has at one first end a male pump connector 270 to be received in the female mini USB port 266 of the pump 218 and, at the other second end, a male phone connector 272 to be removably received within the mini USB port 322 on the smart phone 212.

The wire 274 of the patch cord 220 extends from the pump 218 through the compartment 252 of the cover 216 internally past the tube 229 to exit the right side 234 of the cover 216 through a slotway 276 and then to the USB port 322 on the smart phone port 212. The phone male connector 272 is carried by a flat rectangular plate which carries a number of connector posts 280. The posts 280 are sized to extend from an inner surface of the plate into the slotway 276 in the right side 234 of the cover 216 to removably secure the plate to the cover 216 when the male connector 272 is engaged within the USB port 322 on the smart phone 212. The slotway 276 through the sidewall 234 is preferably sized to permit the pump connector 270 to pass therethrough yet with the plate 278 closing the slotway 276 when the plate 278 is secured to the right side 234 of the cover 216.

The patch cord 220 electrically connects the pump 218 to the smart phone 212 and in so doing provides electrical power to the pump 218 with the smart phone 212 controlling when power is provided to the pump 218. Operation of the pump 218 will dispense fluid from the reservoir 214 out the discharge tube 256 preferably as a jet of liquid. Various features of the smart phone 212 may activate the pump 218. The smart phone 212 preferably has a computerized control application stored in it providing for functionality as may be desired.

The smart phone 212 will communicate activation of the pump 218 by generation a sound 30 by its microphone which will be sensed by one of the sound sensing mechanisms 14.

In one preferred manner of operation, the smart phone 212 may be activated as by activating the smart phone 212 to receive voice commands after a user pushes the convenience key 324. Thereafter, with the smart phone 212 suitably programmed, on a user stating a word such as "dispense", the smart phone 212 would activate the pump 218 so as to dispense an individual dosage of the fluid. To dispense an individual dosage the pump is preferably operated for a set period of time. An individual dose of fluid may, for example, comprise 1 to 3 mm of the alcohol hand cleaner. Rather than merely use voice commands for activation of the pump 218, various other keys on the smart phone 212 could be used, for example, with the smart phone 212 to cause the pump 218 to dispense fluid on a user pushing the convenience key 316. As another example of operation the smart phone 212 could be programmed such that on a user holding down the convenience key 318, the pump would be operated continuously until the key 318 is released. If multiple operations of the pump are carried out then multiple sounds 30 are to be generated by the smart phone.

A preferred pump 218 in accordance with the present invention is a piezoelectric diaphragm micro pump as sold under the trade-mark CurieJet and having dimensions of approximately 25 mm by 24 mm by 10 mm and a pumping capacity of up to about 50 ml/min. Such pumps are described in U.S. Patent Publication US2011/0005606 published Jan. 13, 2011. Other pumps may be used without limitations.

Figure 23:
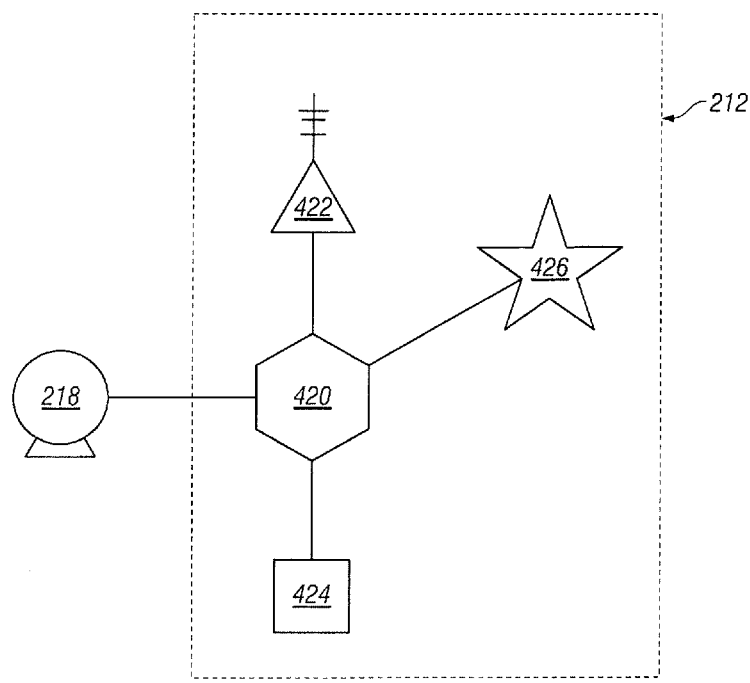
FIG. 23 is a schematic diagram showing the electrically powered components of a personal dispenser assembly of FIG. 21.

Reference is made to FIG. 23 which schematically illustrates the smart phone of FIGS. 20 to 22 as including a computerized controller 420 which is electrically coupled to the pump 218. A battery 424 is shown to provide power to the controller 420 and the other components of the smart phone. A communication module 422 is schematically shown and represents a system for not only generating the sound 30 but also preferably for one or two-way communication of data such as, for example, by well known methods including, for example, Wireless 3G communication as with a cell phone provider, Wi-Fi wireless communication and Bluetooth wireless communication, however, without limit. The various manners of input from a person carrying the cell phone 212 are schematically illustrated by input device 426 and may comprise, for example, manual input via keys, a touch screen and voice commands. It is well known that the controller 420 typically include a data storage system, an ability to store and operate various customized computerized applications, and various timing and clock functions. The data communication module 422 would also include various jacks for hardwiring communication of the controller 420 as to the pump and/or to other peripheral devices such as computer, network hubs and the like.

The pocket-sized personal computer 12 may optionally include a Global Positioning System (GPS) GPS capability such that the location of the personal hand hygiene compliance unit may be determined at any time and communicated as desired to a remote computer. GPS is a space-based global navigation satellite system (GNSS) that provides reliable location and time information. The location of the personal hand hygiene compliance unit can be useful so as, for example, to have the option to select monitoring information based on location, whether, for example, the location is within specific areas in a facility as in high infection risk areas or lower infection risk areas in the facility or whether the personal hand hygiene compliance unit is inside or proximate a facility or remote therefrom. Additionally, insofar as the personal hand hygiene compliance unit is desired to not leave a facility or an area in the facility then, on receiving GPS data that the unit is being moved from a designated area, a warning or alarm may be given as, for example, by an audible warning from the unit and/or a warning to security staff for the facility.

Rather than have GPS enablement, the facility may have a location monitoring system with proximity sensors such as at specific locations or surrounding specific areas as with all access and exit locations for personnel being monitored by such proximity sensors being communication embowered sentry units which communicate with the personal hand hygiene compliance unit should any personal hand hygiene compliance unit be moved proximate thereto or through an access and exit location such that a central computer will be aware of the location or passage of the personal hand hygiene compliance unit as to monitor the same or to issue suitable notices, warnings or alarms based on the location information. As one example, on a personal hand hygiene compliance unit being moved to outside of a facility or an area in a facility, an alarm could be sounded to assist in preventing the unit from being taken away from the facility. The alarm could be generated by the personal hand hygiene compliance unit, or at a location in the facility as at an exit doorway, or could be given to security personnel of the facility. In another example, on a personal hand hygiene compliance unit entering an area of higher infection risk, a notice or warning could be given to the user of the increased risk, or a signal could be generated in or given to the personal hand hygiene compliance unit causing the unit to dispense an increased individual dosage of fluid towards increasing hygiene within an area of higher infection risk or, conversely, a decreased dosage of fluid within an area of lower infection risk.

FIG. 21 illustrates an arrangement in which the pump 218 is an electrical pump powered by the battery 424 of the pocket-sized personal computer 212. It is not necessary that electrical power be provided by the smart phone. The pump 218 in the dispenser may comprise an electrically operated pump which is powered by a battery carried by the sounding dispenser 12, for example, within the cover 216 or in a sealed compartment within the reservoir 214. Where the fluid to be dispensed by the reservoir is alcohol, as a source of power may comprise a fuel cell which uses the fluid to generate power.

Figure 24:
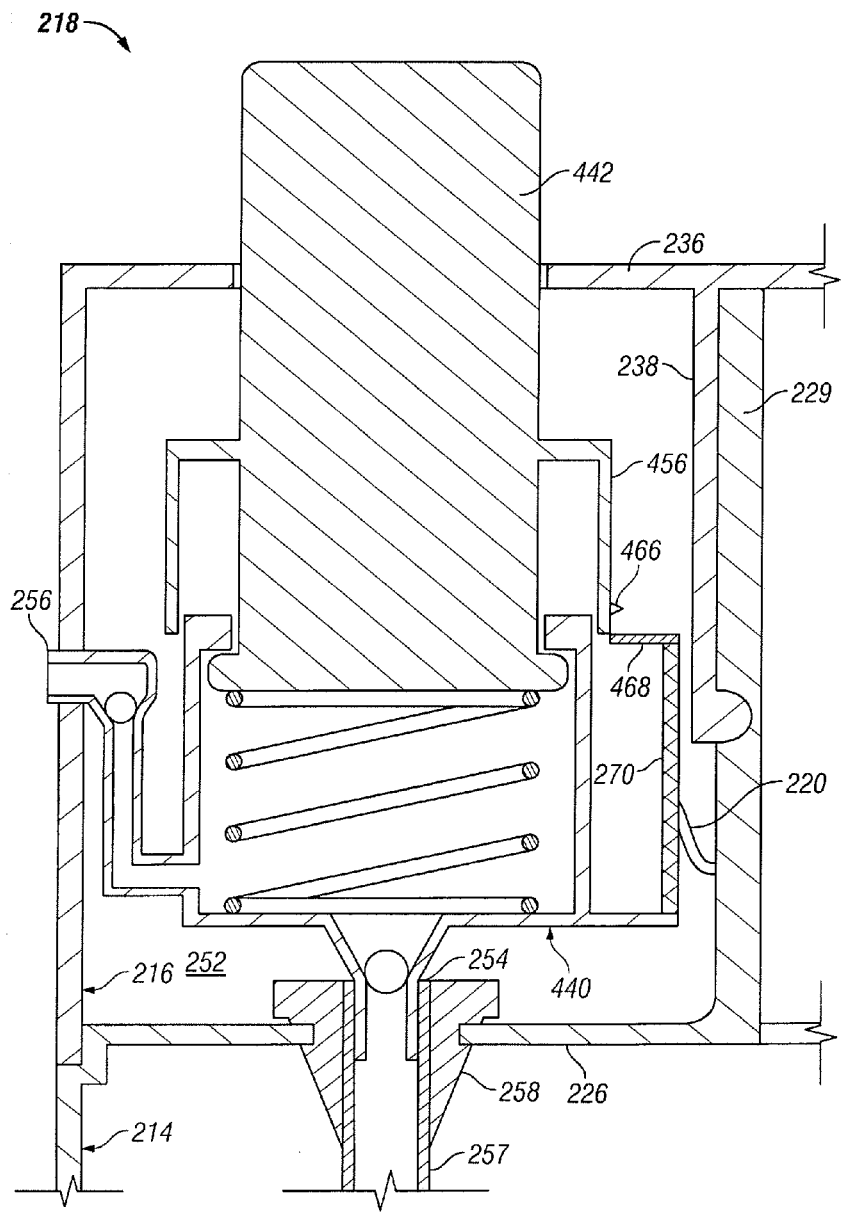
FIG. 24 is a partial vertical cross-sectional rear view similar to that shown in FIG. 14 but of a personal compliance dispenser assembly in accordance with a sixth embodiment to the present invention.

The pump 218 may be a manually operated pump and a patch cord 220 substantially the same as in FIGS. 20 to 23 be used to connect the dispenser and the smart phone. Reference is made to FIG. 24 which shows a partial vertical cross-sectional rear view identical to FIG. 14 with the exception the member 270 on which the sound producing deflectable reed 468 is mounted comprises a pick up device 270 coupled to the patch cord 220. On the piston 442 moving in a stroke of operation, the shoulder 466 engages the reed 468 such that the reed 468 is deflected to produce a sound. The sound is picked up by the pick up device 270 and a signal transferred via the patch cord 220 to the smart phone 212. In the embodiment of FIG. 24, the sound or vibration of the reed 468 could either be picked up by the pick up device 270 acting as an electrically powered sound sensor or vibration sensor or, alternately, the pick up device 270 could with the patch cord be a physical sound guide along or in which sound generated by the reed could be transmitted.

Figure 25:
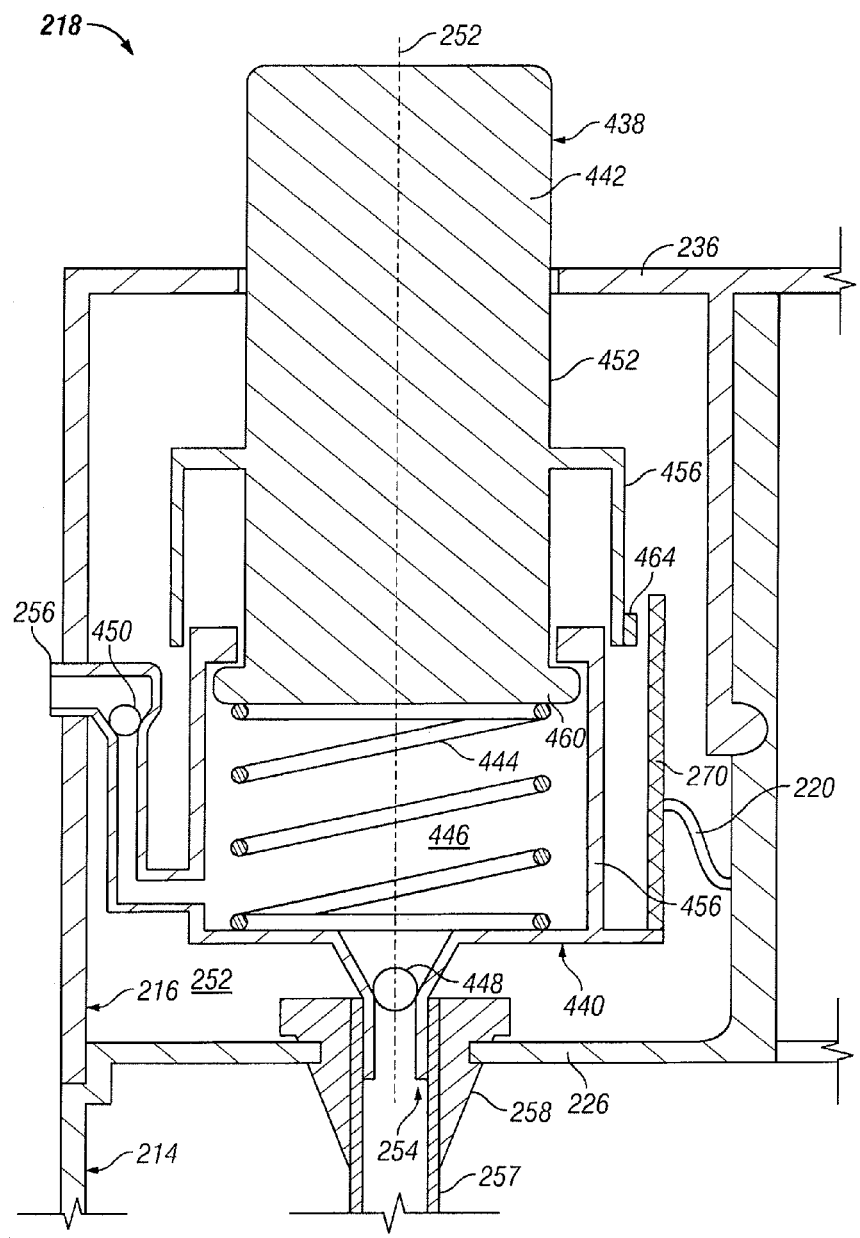
FIG. 25 is a partial vertical cross-sectional rear view similar to that shown in FIG. 24 but of a personal compliance dispenser assembly in accordance with a seventh embodiment to the present invention.

Reference is made to FIG. 25 which shows a partial vertical cross-sectional rear view identical to FIG. 24 with the exception that the shoulder 466 is replaced by a magnet 464 and the sound producing deflectable reed 468 and member 270 are replaced by a magnetic sensor 270 which senses when the magnet 464 on the piston has moved relative the sensor 270 and converts this to an electrical signal transferred to the smart phone via the patch cord 220.

Figure 26:
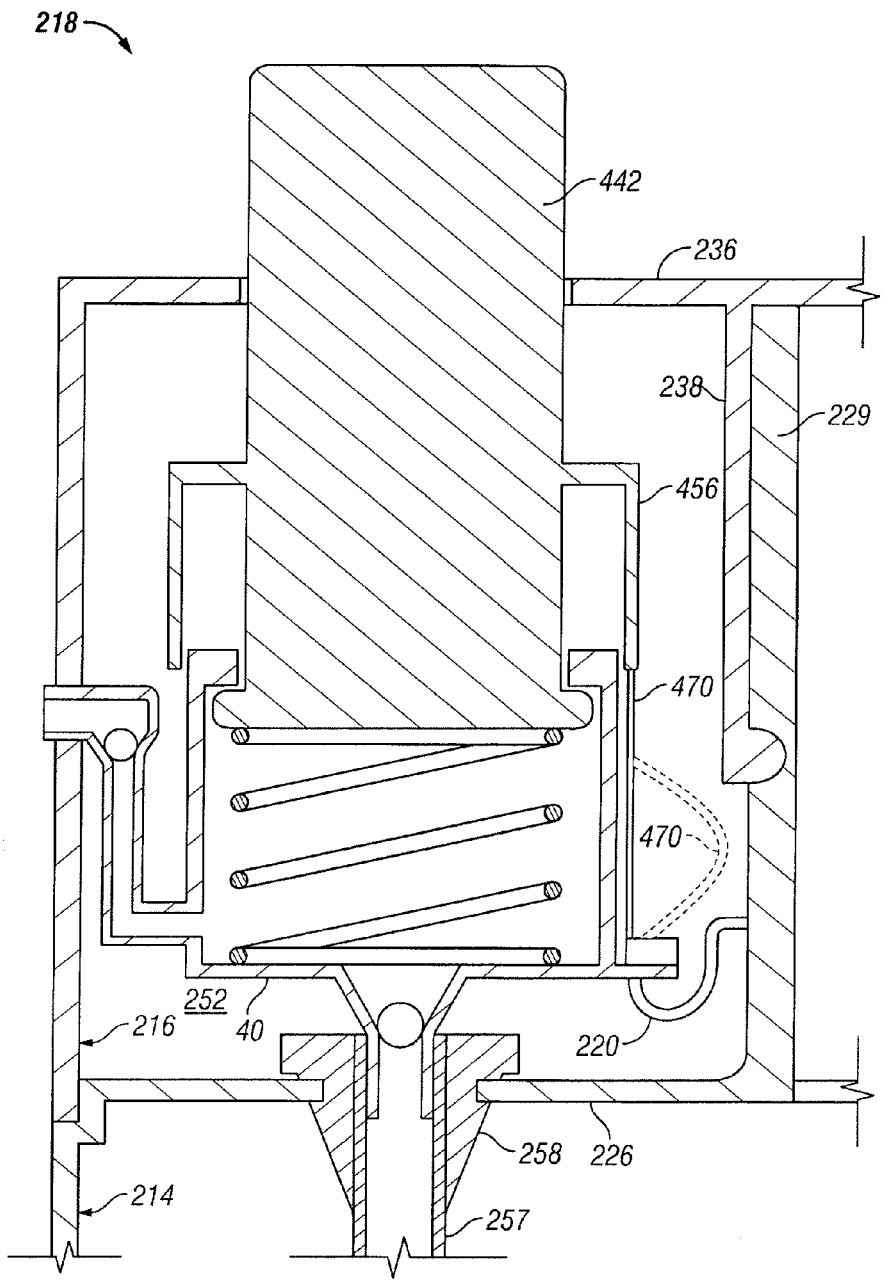
FIG. 26 is a partial vertical cross-sectional rear view similar to that shown in FIG. 24 but of a personal compliance dispenser assembly in accordance with a eighth embodiment to the present invention.

Reference is made to FIG. 26 which illustrates an arrangement identical to the embodiment in FIG. 24 but with the magnet 464 replaced by a piezoelectric generator 470 coupled between the piston 442 and the body 440 for deflection with movement of the piston from a position shown in solid lines in FIG. 25 to a deflected position shown in dashed lines. With such deflection, the generator 470 generates electrical power which is transmitted as a signal to the smart phone by the patch cord 220.

The particular nature of the manual pump 218 to be used is not limited and it may comprise various forms of bellows, piston, peristaltic and other type pumps as are well known to persons skilled in the art.

Personal compliance devices in accordance with the present invention comprising the combination of the fluid dispenser and the communication enabled, personal computer which is to be worn by a user and preferably is pocket-sized, portable and handheld. Therefore, each of the dispenser and the personal computer preferably needs to be of relatively small size and of a shape which facilitates the wearing by a user and a preferred capability to be placed in a wearer's typically sized pocket and, more preferably, have a length not greater than 5", a width not greater than about 3" and a depth not greater than about 2", such that the personal compliance device preferably fits within a volume of 5" by 3" by 2". The personal compliance device is portable and adapted to be handheld.

The personal compliance device preferably includes a communication enabled, personal computer. The personal computer is to be not larger than pocket-sized, that is, preferably not greater than a size which fits in a typically sized pocket of clothing of a wearer so as to preferably fit within such a pocket of a user and, more preferably, have a length not greater than 5", a width not greater than 3" and a depth not greater than 1" such that the pocket-sized personal computer preferably fits within a volume of 5" by 3" by 1". The pocket-sized personal computer is portable and adapted to be handheld.

The pocket-sized personal computer preferably is communication enabled for at least one of wired connectivity and communication with another computer as by USB and wireless communication as by Wi-Fi (trade mark) communication, Bluetooth (trade mark) communication, and IrDA line of sight wireless communication. The Infrared Data Association (IrDA) defines physical specifications communications protocol standards for the short-range exchange of data over infrared light, for uses such as personal area networks (PANs).

The pocket-sized personal computer is preferably enabled with Wi-Fi (trade mark) communication and/or BLUETOOTH (trade mark) communication. With Wi-Fi enablement, connection can be made to other computers such as to a remote host computer and to the Internet when within a range of a wireless network connected to the Internet. Wi-Fi enablement includes various connectivity technologies including wireless local area network (WLAN) and various technologies that support creating personal area network (PAN), local area network (LAN), and wide area network (WAN) connections. BLUETOOTH is a proprietary open wireless technology standard for exchanging data using short wavelength radio transmissions between devices creating personal area networks (PANs).

The pocket-sized personal computer preferably includes data receiving/input capability and at least minimal data storage capability.

The pocket-sized personal computer preferably has at least some capability for output to a wearer preferably with electronic visual display, audio output or vibration and, preferably, capability for at least some input from a wearer preferably by touch as to keys or a touchpad screen or by audible spoken input commands.

While the invention has been described with reference particularly to monitoring dispensers for hand cleaning fluids, the invention is not so limited and can be used to monitor usage of dispensers of almost any type of product.

While the invention has been described with reference to preferred embodiments, many modifications and variations will now occur to persons skilled in the art. For a definition of the invention, reference is made to the following claims.

We claim:

1. A system for monitoring activation of a fluid dispenser comprising a fluid dispenser for dispensing fluid and a sound sensing mechanism remote from the fluid dispenser,
the fluid dispenser dispensing fluid when activated by a user,
the fluid dispenser includes a fluid pump for dispensing fluid on movement of an actuator activated by the user,
the fluid dispenser including a sound generator which generates a sound when the fluid dispenser is activated by the user,
the sound generator comprises an air whistle which produces the sound from a stream of pressurized air, the fluid dispenser includes an air pump for pressurizing air on movement of the actuator and delivering the stream of pressurized air to the air whistle, the sound sensing mechanism separate from and spaced from the fluid dispenser, the sound sensing mechanism including a sound sensor to sense the sound generated by the sound generator, the sound sensing mechanism including a communication mechanism to transmit data representative of the sound sensed by the sound generator to a remote computer.

2. The system as claimed in claim 1 wherein the fluid dispenser is a manually operated dispenser in which the actuator is moved by the user to dispense fluid.

3. The system as claimed in claim 1 in which the fluid pump is a piston pump in which a piston element is reciprocally movable relative to a piston chamber forming body in a cycle of operation including an instroke and an outstroke to alternatively in one of the instroke and outstroke draw fluid from a fluid reservoir into the fluid pump and in the other of the instroke and the outstroke discharge fluid from the fluid pump, the air pump formed between the piston element and the piston chamber forming body for drawing air into the air pump in a first of the instroke and the outstroke and to pressurize air in a second of the instroke and the outstroke.

4. The system as claimed in claim 1 further including a monitoring system including a plurality of said fluid dispensers, a plurality of said sound sensing mechanisms located to sense the sound from the fluid dispensers and the remote computer is a central computer for receiving the data transmitted from the plurality of said sound sensing mechanisms for monitoring.

5. The system as claimed in claim 4 wherein at least one of the sound sensing mechanisms is a computing device having a computer housing, and within the computer housing a controller, a user interface, a battery, the sound sensor and the communication mechanism, wherein the controller monitors when the sound is sensed and controls the communication mechanism to transmit data regarding the activation of the fluid pump to the central computer.

6. The system as claimed in claim 5 wherein the communication mechanism includes a generator of sound which generates a sound signal which represents the data, which said sound signal represents the data that is sensed by one of the plurality of the said sound sensing mechanisms.

7. The system as claimed in claim 5 wherein the communication mechanism providing for WiFi transmission of the data to the central computer.

8. The system as claimed in claim 1 including a personal hand hygiene unit carried on a person, the personal hand hygiene unit comprising a dispenser of a hand sanitizing fluid carried on the person physically coupled to a communication enabled, portable handheld pocket-sized personal computing device also carried on the person, the computing device having a controller, a battery and a generator of sound, the controller monitoring when the dispenser of the hand sanitizing fluid dispenses fluid and generating a sound signal with the generator of sound when the dispenser of hand sanitizing fluid dispenses fluid, the sound signal capable of being sensed by the sound sensing mechanism.

9. The system as claimed in claim 8 wherein:

the dispenser of the hand sanitizing fluid comprising a dispenser housing, a reservoir for containing the fluid, a pump and a discharge outlet, the pump coupled to the reservoir with the pump in communication with the fluid in the reservoir, the pump capable of being activated to dispense the fluid from the reservoir out the discharge outlet, the computing device having a computer housing, and within the computer housing the controller, a user interface, a battery and the generator of sound, the controller monitoring when the pump is activated and generating the sound signal with the generator of sound when the pump is activated.

10. The system as claimed in claim 9 wherein the dispenser housing is mechanically coupled to the computer housing.

11. The system as claimed in claim 4 wherein the sound sensing mechanism transmitting the data as WiFi wireless signals, the system including one or more WiFi wireless router connected to the central computer, the WiFi wireless router receiving WiFi wireless signals and relaying the WiFi wireless signals to the central computer.

12. A method of compliance monitoring of hand washing within a facility comprising:

providing a plurality of fluid dispensers within the facility, wherein each fluid dispenser includes a fluid pump for dispensing fluid on movement of an actuator, an air whistle which produces sound from a stream of pressurized air and an air pump for pressurizing air on movement of the actuator and delivering the stream of pressurized air to the air whistle, providing a plurality of sound sensors spaced within the facility, producing a sound each time each of the fluid dispenser is activated by delivering the stream of pressurized air from the air pump to the whistle, remotely monitoring each sound produced by each dispenser with one or more sound sensors, and transmitting data representative of the sounds sensed by each sound sensors to a central computer.

13. A method as claimed in claim 12 including:

providing a plurality of WiFi wireless routers within the facility, providing the wireless routers to be connected to the central computer, transmitting data representative of the sounds sensed by each sound sensor as a WiFi wireless signal to one of the WiFi wireless routers, transmitting the data received by each of the WiFi wireless routers to the central computer.

14. The system as claimed in claim 3 wherein the fluid dispenser is a manually operated dispenser in which the actuator is moved by the user to dispense fluid.

15. The system as claimed in claim 4 wherein the fluid dispenser is a manually operated dispenser in which the actuator is moved by the user to dispense fluid.

16. The system as claimed in claim 1 wherein:

the fluid dispenser further comprises a dispenser housing, a reservoir for containing the fluid, the fluid pump and a discharge outlet, the fluid pump coupled to the reservoir with the fluid pump in communication with the fluid in the reservoir, the fluid pump capable of being activated to dispense the fluid from the reservoir out of the discharge outlet.

17. The system as claimed in claim 8 wherein the fluid dispenser is a manually operated dispenser in which the actuator is moved by the user to dispense fluid.

* * * * *